United States Patent
Hauser et al.

(10) Patent No.: US 6,966,992 B2
(45) Date of Patent: Nov. 22, 2005

(54) METHOD OF PURIFICATION OF MOLECULES USING UNBRANCHED TERMINAL ALKYLDIOLS

(75) Inventors: Terry Allen Hauser, Winston-Salem, NC (US); Kirk James Hayenga, Raleigh, NC (US)

(73) Assignee: Akzo Nobel NV, Arnhem (NL)

( * ) Notice: Subject to any disclaimer, the term of this patent is extended or adjusted under 35 U.S.C. 154(b) by 527 days.

(21) Appl. No.: 09/813,093

(22) Filed: Mar. 19, 2001

(65) Prior Publication Data

US 2002/0183483 A1 Dec. 5, 2002

(51) Int. Cl.⁷ .............................................. B01D 15/08
(52) U.S. Cl. .................... 210/656; 210/635; 210/198.2; 210/500.34; 210/500.35; 560/1; 560/352; 930/120; 530/344
(58) Field of Search .................................. 210/635, 656, 210/198.2, 500.34, 500.35; 560/1, 852; 930/120; 530/344

(56) References Cited

U.S. PATENT DOCUMENTS

| 5,693,769 A | * | 12/1997 | Kahne et al. ................... 536/5 |
| 5,801,039 A | * | 9/1998 | Maurer et al. ............... 435/221 |
| 5,994,511 A | * | 11/1999 | Lowman et al. ......... 530/387.3 |
| 6,008,041 A | * | 12/1999 | Frye et al. ................... 435/325 |
| 6,437,101 B1 | * | 8/2002 | Hayenga et al. ............ 530/399 |

OTHER PUBLICATIONS

Varkey et al. J. Peptide Res. 51, 49–54 (1998).*
Yu et al. J. Chromatography A, 725, 149–155(1996).*
Arakawa et al. Arch. Biochem. Biophys. 224(1):169–177 (1983).*

* cited by examiner

Primary Examiner—Robert A. Wax
(74) Attorney, Agent, or Firm—William P. Ramey, III

(57) ABSTRACT

The current invention provides methods for molecule purification by RP-LC and RP-HPLC that uses unbranched terminal alkyldiols as eluting solvents. In particular, the present invention purifies molecules, particularly proteins and peptides, on reverse phase liquid chromatography columns using a buffer containing either 1,5 pentanediol, 1,6 hexanediol or 1,7 heptanediol.

22 Claims, 29 Drawing Sheets

Lane 1 - Mark 12 MW markers
Lane 2 - Bakerbond butyl fraction # 8
Lane 3 - Bakerbond butyl fraction #22
Lane 4 - Bakerbond butyl fraction #29

Lane 1 - Mark 12 MW markers
Lanes 2-9 - Not applicable
Lane 10 - CG71M Step Elution at 32% 1,6 hexanediol

Attachment 3
062-32 SDS-PAGE Analysis of
Various Experiments

Gel 1

1 2 3 4 5 6 7 8 9 10

Gel 2

1 2 3 4 5 6 7 8 9 10

Lane 1 - Mark 12 MW markers
Lane 2 - NA
Lane 3 - NA
Lane 4 - NA
Lane 5 - CG71C Low pH f # 19
Lane 6 - CG71C Low pH f #21
Lane 7 - CG71C Low pH f # 27
Lane 8 - CG71C Low pH f #35
Lane 9 - CG71C Low pH f #40
Lane 10 - NA Lane 1 - Mark 12 MW Markers
Lane 2 - CG71C Low pH f #47
Lane 3 - CG71C Low pH f #51
Lane 4 - CG71C Low pH f #58
Lane 5 - CG71C pH 7.2 f #17
Lane 6 - CG71C pH 7.2 f #20
Lane 7 - CG71C pH 7.2 f #23
Lane 8 - CG71C pH 7.2 f #27
Lane 9 - CG71C pH 7.2 f #30
Lane 10 - Blank

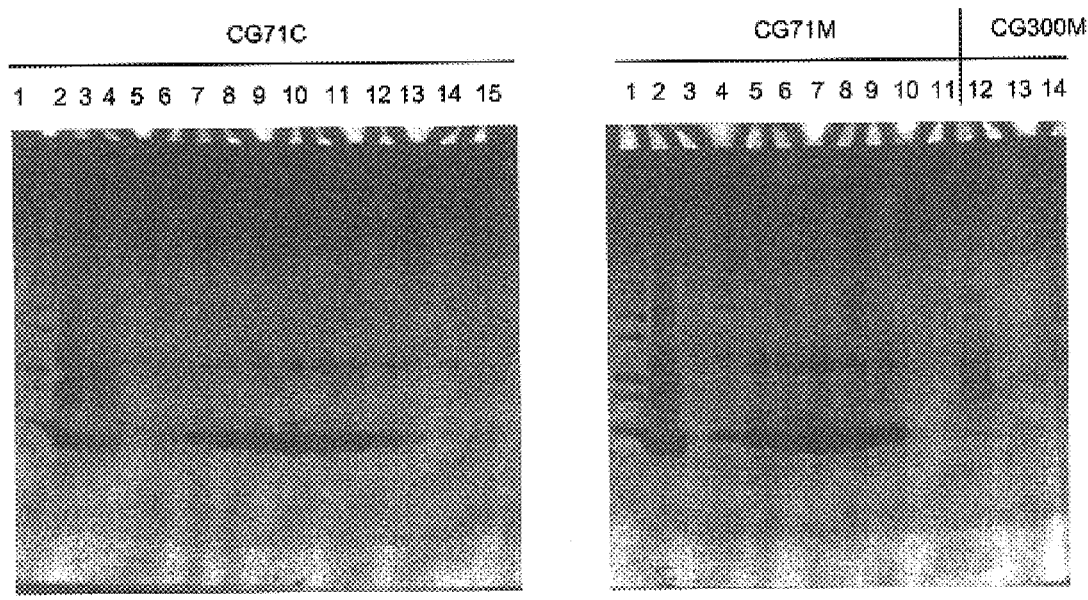

Lane 1 - Mark 12 MW Markers
Lane 2 - Top Phase containing crude material
Lane 3 - fraction # 4 (Flow Through)
Lane 4 - fraction # 9
Lane 5 - fraction # 10
Lane 6 - fraction # 11
Lane 7 - fraction # 12
Lane 8 - fraction # 13
Lane 9 - fraction # 14
Lane 10 - fraction # 15
Lane 11 - fraction # 16
Lane 12 - fraction # 17
Lane 13 - fraction # 20
Lane 14 - fraction # 21
Lane 15 - fraction # 22

Lane 1 - Mark 12 MW Markers
Lane 2 - Top Phase containing crude material
Lane 3 - fraction # 9 (CG71M)
Lane 4 - fraction # 10
Lane 5 - fraction # 11
Lane 6 - fraction # 12
Lane 7 - fraction # 13
Lane 8 - fraction # 14
Lane 9 - fraction # 15
Lane 10 - fraction # 20
Lane 11 - fraction # 21
Lane 12 - fraction # 4 (CG300M)
Lane 13 - fraction # 9
Lane 14 - fraction # 10

FIG. 13

Lane 1 - Mark 12 MW Markers
Lane 2 - Top Phase of crude mixture
Lane 3 - fraction # 2
Lane 4 - fraction # 3
Lane 5 - fraction # 4
Lane 6 - fraction # 5
Lane 7 - fraction # 6
Lane 8 - fraction # 7
Lane 9 - fraction # 8
Lane 10 - fraction # 19
Lane 11 - fraction # 20
Lane 12 - fraction # 21
Lane 13 - fraction # 22
Lane 14 - fraction # 23
Lane 15 - blank

METHOD OF PURIFICATION OF MOLECULES USING UNBRANCHED TERMINAL ALKYLDIOLS

1. FIELD OF THE INVENTION

The present invention relates to a method for purifying molecules with unbranched terminal alkyldiols. In particular, the method of the invention is useful for purifying molecules, particularly proteins and peptides, on reverse phase liquid chromatography columns using a buffer containing 1,5 pentanediol, 1,6 hexanediol or 1,7 heptanediol.

2. BACKGROUND OF THE INVENTION

Proteins and peptides play critical roles in metabolism, gene expression, signal transduction, cellular and extracellular structures, which are essential to the survival and/or reproduction of any living organism. Many proteins and peptides are useful in therapeutic and/or diagnostic applications, particularly, when available in pure form. Contaminants often prevent realization of therapeutic and/or diagnostic goals and may endanger the health of a patient.

Protein purification or peptide purification is a significant challenge, especially when large amounts of material are required for therapeutic or diagnostic purposes. Procedures that simply and rapidly provide the protein or peptide of interest in pure form and good yield are highly desirable, regardless of scale.

Frequently, proteins and peptides are produced by recombinant DNA techniques because large amounts of heterologous material can be expressed in bacteria or other host cells. As is well known in the art, recombinant DNA techniques involve transfecting host cells with DNA encoding the protein and growing the cells under conditions favoring expression of the heterologous protein (see, e.g., U.S. Pat. Nos. 4,565,785, 4,673,641, 4,378,921).

Human growth hormone ("hGH") and antagonists for hGH, (i.e., growth hormone antagonists ("GHA")) are examples of proteins that can be used in a number of therapeutic applications and that have been produced by recombinant methods. Human growth hormone has been used for the treatment of hypopituitary dwarfism and all conditions resulting from low levels of hGH production, whether such condition is caused by genetic defect, injury or hypophysectomy. Human growth hormone can also improve the recovery rate of burn victims and other hospitalized patients. GHA, on the other hand, has been used to treat acromegaly, a form of gigantism caused by overproduction of hGH (Kopchick et al., U.S. Pat. Nos. 5,681,809, 5,958, 879, 5,350,836). Other possible medical uses of GHA are the prevention of retinopathy in diabetes patients and the treatment of cancer patients with tumors overexpressing receptors that bind growth hormone (Clark et al., 1996, WO97/11178).

Reverse phase liquid chromatography ("RP-LC") and reverse phase high-performance liquid chromatography ("RP-HPLC") are commonly used to purify molecules such as peptides and proteins, produced by either synthetic or recombinant methods. RP-LC and RP-HPLC methods can efficiently separate closely related impurities and have been used to purify many diverse molecules (Lee et al., "Preparative HPLC," 8$^{th}$ Biotechnology Symposium, Pt. 1, 593–610 (1988)). Further, RP-LC and RP-HPLC have been successfully used to purify molecules, particularly, proteins on an industrial scale (Olsen et al., 1994, *J. Chromatog. A*, 675, 101).

Typical eluants for RP-LC and RP-HPLC are ethanol, isopropanol, methanol and acetonitrile. Acetonitrile has been used in the purification of proteins such as insulin (Kroeff et al., 1989, *J. Chromatography*, 461, 45). However, these solvents are all highly flammable and toxic, which presents a significant safety issue when used on a large scale. Further, acetonitrile frequently has a denaturing effect when used as an eluant for reverse phase chromatography. Disposal of toxic organic solvents, particularly on a process scale, entails significant expenditure.

Thus, there is a need in the art for procedures that selectively separate molecules such as peptides, polypeptides (e.g., hGH and GHA) and organic compounds from impurities by RP-LC and RP-HPLC using inflammable solvents that are less toxic, cheaper and less denaturing than typical solvents used as eluants in RP-LC and RP-HPLC

3. SUMMARY OF THE INVENTION

The current invention provides methods for purifying molecules by RP-LC and RP-HPLC that uses unbranched terminal alkyldiols as eluting solvents. In particular, the present invention purifies molecules, particularly proteins and peptides, on reverse phase liquid chromatography columns using a buffer containing 1,5 pentanediol, 1,6 hexanediol or 1,7 heptanediol. These non-flammable terminal alkyldiols are less toxic, cheaper and less denaturing than typical solvents used as eluants in RP-LC and RP-HPLC.

In one aspect, the current invention provides a method for purifying a molecule from a mixture. First, the mixture is loaded onto a reverse phase liquid chromatography column. Second, the molecule is eluted from the column with a buffer containing a diol, which is 1,5 pentanediol, 1,6 hexanediol or 1,7 heptanediol. In a preferred embodiment, the diol is 1,6 hexanediol. In another preferred embodiment, the column is a high pressure reverse phase liquid chromatography column.

Preferably, the buffer is at a pH between about 2.0 and about 12.0. More preferably, the buffer is at a pH between about 7.0 and about 11.0, most preferably, between about 6.0 and about 8.0. Preferably, the concentration of 1,6 hexanediol in the buffer is between about 0% and about 80%. More preferably, the concentration of 1,6 hexanediol in the buffer is between about 0% and about 50%.

In one embodiment, the molecule is a polypeptide. Preferably, the polypeptide is hGH or GHA. In a preferred embodiment, the polypeptide is GHA. In another preferred embodiment, the polypeptide is human growth hormone. In another embodiment, the molecule is a peptide. Preferably, the peptide is α-MSH, enkephalin, somatostatin or somatotropin.

In one embodiment, the column is a high performance liquid chromatography column. In another embodiment, the column is a preparative column. Preferably, the column has a diameter of between about 5 cm and about 2.0 m, more preferably, between about 10 cm and about 100 cm.

Preferably, the column includes a polymeric resin. In one preferred embodiment, the polymeric resin is styrene divinylbenzene (i.e., styrenic). In another preferred embodiment, the polymeric resin is methacrylate or acrylic.

In one embodiment, the mixture is loaded on the column at about 10.0 g molecule/liter bed volume. In another embodiment, the molecule is further purified after RP-LC fractionation.

4. BRIEF DESCRIPTION OF THE DRAWINGS.

FIG. 13 illustrates SDS-PAGE analysis of the eluate of FIGS. 10 and 11.

5. DETAILED DESCRIPTION OF THE INVENTION

Figure 1:
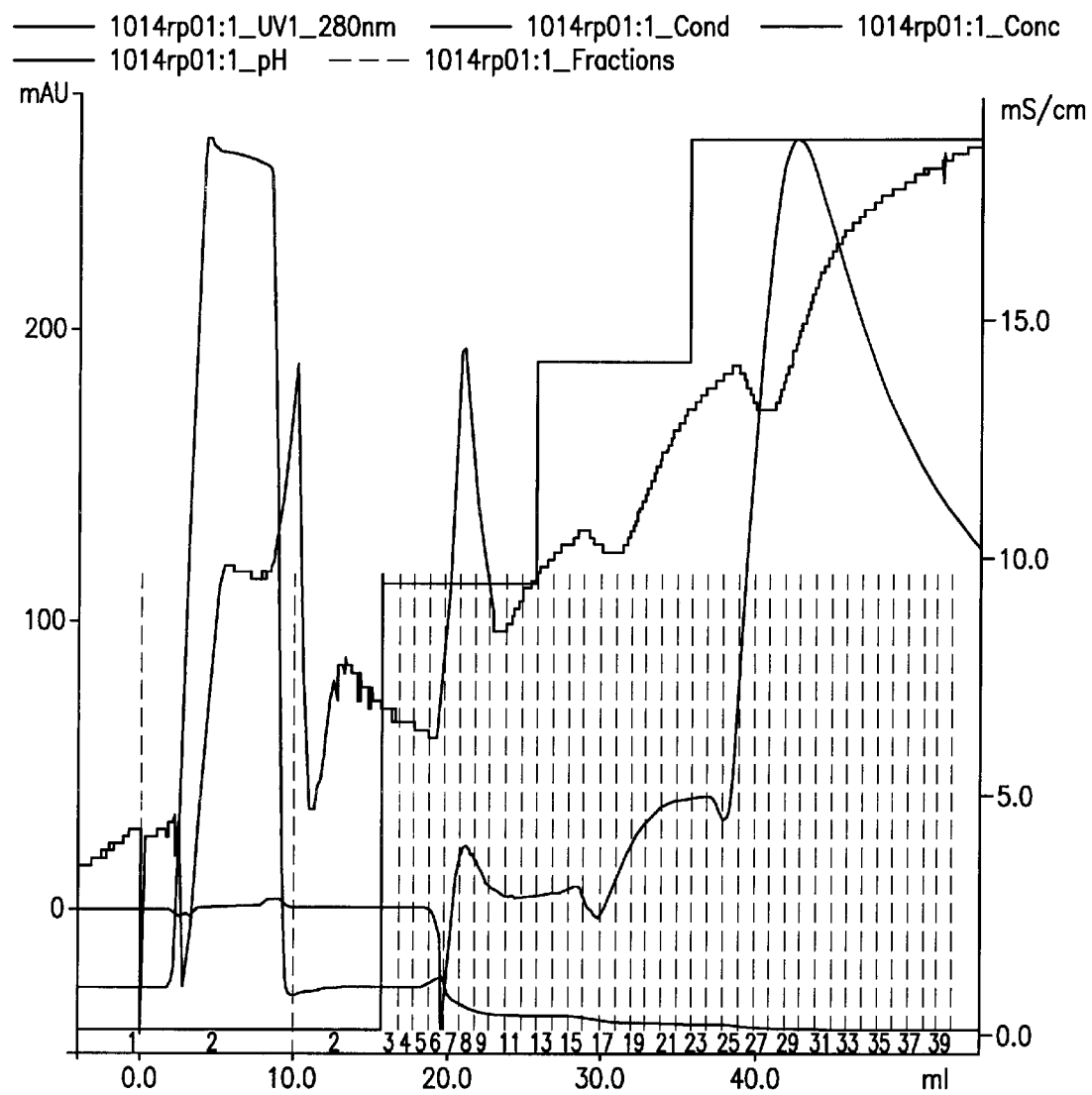
FIG. 1 illustrates the elution profile of GHA from a WP-butyl column using a gradient of 0%–60% 1,6 hexanediol in 50 mM Tris HCl, pH 7.2.

The present invention relates to methods for purifying molecules using linear terminal alkyldiols. The details for practicing the invention are described in the subsections below.

5.1 DEFINITIONS

As used herein, "molecule" refers to a peptide, a polypeptide or a non-peptidyl compound.

As used herein, "peptide" refers to a molecules of up to about thirty covalently attached amino acids including natural and unnatural amino acids of the L isomeric form or D isomeric form as well as derivatives and/or analogues thereof. Examples of peptides include molecules such as enkephalin, somatostatin and A-MSH. Other peptides that can be purified using the method of the current invention, include but are not limited to, the list of bioactive peptides listed in a catalog obtainable from Bachem Biosciences Limited (Philadelphia, Pa.).

As used herein, "polypeptide" refers to peptides having more than thirty amino acids and includes both endogenous and exogenous (i.e., heterologous) polypeptides. Examples of proteins include, but are not limited to, human growth hormone and growth hormone antagonist.

As used herein "non-peptidyl compound" refers to an organic or inorganic compound having a molecular weight of between about 200 and 800 Daltons. The compound is preferably an organic compound. Particularly preferred organic compounds are antibiotics such as vancomycins, cephalosporins, penicillins and the like.

As used herein "growth hormone antagonist ("GHA")" refers to antagonists of human growth hormone. GHA has growth inhibitory or other human growth hormone antagonizing effects. GHA may be used to reduce the activity of human growth hormone in a human suffering from diabetes, diabetic retinopathy, diabetic nephropathy, growth hormone tumor, acromegaly or gigantism.

As used herein, "buffer" refers to a solution that resists changes in pH through acid-base conjugate components. Suitable free acids for forming buffers include citric, acetic, phosphoric, maleic, malonic, phthalic, salicyclic, fumaric, dimethyl malonic, mandelic, malic, formic, tartaric, itaconic, lactic, barbituric, ascorbic, 2,2 dimethyl succinic, succinic, benzoic, propionic, etc. Suitable free bases for forming buffers include Tris, triethylamine, imidazole, brucine, tricine, glycinamide, histidine, ethanolamine, glycine, ethylamine, dimethylamine, etc. Those of skill in the art will recognize that many other acids and bases can be used to prepare buffers. Preferred buffers typically have a pH between about 2.0 and about 12.0.

5.1 SOURCES OF MOLECULES

Molecules may be prepared by any art-known technique. Thus, for example, proteins or peptides may be obtained by culturing procaryotes that secrete either wild-type or heterologous protein or peptide, lysis of procaryotes, lysis of procaryotes that express heterologous protein or peptides, lysis of eucaryotes, lysis of eucaryotes expressing heterologous protein or peptide, growing eucaryotes that secrete soluble protein or peptide, total synthesis, etc. Organic or inorganic molecules may be prepared using well-known synthetic methods and procedures known to the skilled artisan. Molecules, if commercially available, may be purchased from well known chemical suppliers (e.g., Alfa Aesar (Wardhill, Mass.), Merck KgaA (Darmstadt, Germany), etc.)

Procaryotes can provide proteins or peptides after cell lysis. A number of methods may be used to lyse bacterial cells such as bead mills, osmotic shock, freeze fracture and enzymatic treatment. Preferably, a high pressure homogenizer, such as a Microfluidizer, is used to lyse bacterial cells. Alternatively, microorganisms that secrete either wild type or heterologous protein or peptide may be cultured to provide proteins or peptides. Wild-type prokaryotic cells or those expressing heterologous proteins, can be grown under a variety of conditions known to the skilled artisan. Methods of growing inocula and inoculating culturing medium are known to the skilled artisan and exemplary methods have been described in the art. Preferred media, times, temperatures and pH for culturing microorganisms are also known in the art. Thus, for example, the cells may be grown in a medium suitable for growth of such cells, for example, minimal media or complete (i.e., rich) media.

Heterologous proteins may be advantageously produced by recombinant DNA technology using techniques well known in the art for expressing genes. These methods include, for example, in vitro recombinant DNA techniques, synthetic techniques and in vivo genetic recombination. See, for example, the techniques described in Sambrook et al., "Molecular Cloning," Cold Spring Harbor Laboratory Press, Cold Spring Harbor, N.Y., Vols. 1–3: (1989), and periodic updates thereof, and Ausubel et al., eds., 1989, "Current Protocols in Molecular Biology," Green Publishing Associates, Inc., and John Wiley & Sons, Inc., New York. DNA and RNA encoding any heterologous protein may be chemically synthesized using, for example, synthesizers. See, for example, the techniques described in "Oligonucleotide Synthesis," 1984, Gait, M. J. ed., GIRL Press, Oxford.

A variety of host-expression vector systems may be utilized to express proteins. The expression systems that may be used for purposes of the invention are microorganisms such as bacteria (e.g., E. coli, B. subtilis) transformed with recombinant bacteriophage DNA, phagemid DNA or cosmid DNA expression vectors containing a nucleotide sequence encoding the desired protein; yeast (e.g., Saccharomyces, Pichia) transfected with recombinant yeast expression vectors containing a nucleotide sequence encoding the protein of interest; insect cell systems infected with recombinant virus expression vectors (e.g., baculovirus) containing a nucleotide sequence encoding the protein of interest; plant cell systems infected with recombinant virus expression vectors (e.g., cauliflower mosaic virus, CaMV; tobacco mosaic virus, TMV) or transfected with recombinant plasmid expression vectors (e.g., Ti plasmid) containing a nucleotide sequence encoding the protein of interest; or mammalian cell systems (e.g., COS, CHO, BHK, 293, 3T3, U937) harboring recombinant expression constructs containing promoters derived from the genome of mammalian cells (e.g., metallothionein promoter) or from mammalian viruses (e.g. the adenovirus late promoter; the vaccinia virus 7.5K promoter).

In eukaryotic systems, a number of selection systems may be used, such as for example, the herpes simplex virus thymidine kinase (Wigler et al., 1977, Cell, 11, 223), hypoxanthine-guanine phosphoribosyltransferase (Szybalska et al., 1962, Proc. Natl. Acad. Sci., USA 48, 2026), and adenine phosphoribosyltransferase (Lowy et al., 1980, Cell, 22, 817) genes can be employed in tk⁻, hprt⁻ or aprt⁻ cells, respectively. Also, antimetabolite resistance can be used as the basis of selection for the following genes: dhfr, which confers resistance to methotrexate (Wigler et al., 1980, Proc. Natl. Acad. Sci., USA 77, 3567; O'Hare et al., 1981, Proc. Natl. Acad. Sci., USA 78, 1527); gpt, which confers resistance to mycophenolic acid (Mulligan et al., 1981, Proc. Natl. Acad. Sci. USA 78, 2072); neo, which confers resistance to the aminoglycoside G-418 (Colberre-Garapin et al., 1981, J. Mol. Biol. 150, 1); and hygro, which confers resistance to hygromycin (Santerre et al., 1984, Gene, 30, 147).

In bacterial systems, as previously mentioned, a number of expression vectors may be selected. Bacteria suitable for the practice of the invention are gram positive and gram negative bacteria. In a preferred embodiment, soluble protein solutions are obtained by expression of heterologous proteins in Eschericia coli ("E. coli") and subsequent cell lysis. The protein can be expressed in a procaryotic cell using expression systems known to those of skill in the art of biotechnology. Expression systems useful for the practice of the current invention are described in U.S. Pat. Nos. 5,795,745; 5,714,346; 5,637,495; 5,496,713; 5,334,531; 4,634,677; 4,604,359; and 4,601,980.

Procaryotic cells can be grown under a variety of conditions known to the skilled artisan. In one aspect of the current invention, the cells are grown in a medium suitable for growth of such cells, for example, minimal media or complete (i.e., rich) media.

5.2. PURIFICATION OF MOLECULES USING TERMINAL ALKYLDIOLS

The first step of the current invention entails loading a mixture containing a molecule on a reversed-phase liquid chromatography column. The mixture may contain a number of biological components such as carbohydrates, lipids, proteins and nucleic acids. The mixture may also contain closely related isomers of the molecule, such as regioisomers, geometric isomers, stereoisomers, etc.

The molecule may be a peptide, polypeptide or organic molecule (e.g., an antibiotic) Preferred peptide molecules are enkephalin, somatostatin, somatropin, and α-MSH. Other molecules that can be purified using the method of the current invention include, but are not limited to, the list of bioactive peptides available from Bachem Biosciences Inc., (Philadelphia, Pa.). Thus, atrial natriuretic peptides, basic fibroblast inhibitory peptides, bradykinins, corticolropin inhibiting peptides and the like, are examples of molecules that can be purified using the method of the current invention.

Preferred protein molecules are GHA and hGH. Other proteins that can be purified using the method of the current invention include, but are not limited to, blood clotting factors, Factor VIII, relaxin, insulin-like growth factors, interferons, tPA, antibodies, surface antigens for viral vaccines, animal growth factors derived for example from porcine, bovine or ovine sources, insulin, erythropoietin, granulocyte-macrophage colony stimulating factor, IGF-2, interluekins and other cytokine, soluble receptors, soluble selecting, heregulin, vascular endothelial growth factor, epidermal growth factors ("EGF"), EGF like growth factor, epithelial transforming growth factor, keratinocyte growth factor, tumor necrosis factor transforming growth factors, thrombopoietin, etc. Preferred organic molecules include antibiotics such as vancomycin, cephalosporin C, penicillin G and penicillin V. Other organic molecules that can be purified using the method of the current invention include, but are not limited to, polyene macrolides, terpenes, alkaloids, carbohydrates, polyketides, etc.

The column may be low-pressure, medium pressure or high-pressure, the latter of which is packed with a medium having a particle diameter less than about 20 $\mu$m. Preferably, for preparative scale purification the column is a low pressure column. Preferably, the column is packed with a medium having a particle diameter between about 1 $\mu$m to about 300 $\mu$m, more preferably, between about 15 $\mu$m to about 120 $\mu$m and most preferably, between about 35 $\mu$m to about 120 $\mu$m. Preferably, the column medium has a pore size between about 0 Å to about 1000 Å, more preferably between about 150 Å to about 300 Å. Thus, both non-porous (i.e., non-porous polymeric beads) and porous media can be used to pack RP-LC columns.

The column resin may be any suitable hydrophobic material including, but not limited to, polymeric resins such as polystyrene divinylbenzene resins (e.g., CG-300, CG-1000 or CG-161), acrylate resins or methacrylate resins (e.g., CG-71-C or CG-71-M), silica-based resins (e.g., silica with a C1–C18 alkyl group, phenyl derivatives, aminoalkyl or aminophenyl compounds), agarose-based resins (e.g., agarose with a C1–C18 alkyl group or phenyl derivatives), sepharose-based resins (e.g., sepharose with a C1–C18 alkyl group or phenyl derivatives) and superose-based resins (e.g., superose with a C1–C18 alkyl group or phenyl derivatives). Those of skill in the art will appreciate that many other hydrophobic adsorbents are known in the art and may be used in the current invention. Column resin may be purchased from a number of suppliers such as, for example, Bayer Corporation (Morris Township, N.J.), Serva (Heidelberg, Germany), Alltech Associates, Inc. (Deerfield, Ill.) TosoHaas (Montgomery, Pa.), Pharmacia (Piscataway, N.J.), The Separations Group, Inc. (Hesperia, Calif.), Waters Corporation (Milford, Ma.), Bio-Rad Laboratories (Hercules, Calif.) and Polymer Labs (Church Stretton, Shropshire, England). The type of resin used to purify a molecule may be readily determined by those of ordinary skill in the art and will depend on factors such as the nature of the molecule, the level of purity required, the amount of purified molecule required, etc.

The column may be an analytical or preparative column. The amount of molecule loaded onto the column is generally between about 0.01 g molecule/liter bed volume to about 70.0 g molecule/liter bed volume, preferably, between about 0.02 g molecule/liter bed volume to about 40.0 g molecule/ liter bed volume, more preferably, between about 0.05 g molecule/liter bed volume to about 30.0 g molecule/liter bed volume, even more preferably, between about 1.0 g molecule/liter bed volume to about 25.0 g molecule/liter bed volume and most preferably, between about 3.0 g molecule/ liter bed volume to about 15.0 g molecule/liter bed volume. In a preferred embodiment, the amount of molecule loaded onto the column is about 10.0 g molecule/liter bed volume. Generally, the lower limit for loading is the ability to detect product eluting from the column media, while the highest limit for loading is the saturation capacity of the resin. It should be noted that the above amounts are general guidelines only and will depend on experimental factors such as the nature of the molecule, flow rate, resin type and the like.

In a preferred embodiment, the column is a preparative column, meaning preparative scale and/or preparative load.

The column diameter is preferably, between about 5 cm and about 2 m, more preferably, between about 10 cm and about 100 cm.

The column length must be scaled properly to the column diameter. In general, this is an empirical determination that may be readily made by those of skill in the art. Factors which may be important in determining the relationship between column diameter and column length include bead size, type of elution (e.g., isocratic vs. gradient elution), resin type (e.g., ion exchange columns are short and size exclusion columns are longer; the two columns vary in length because of different modes of separation), desired processing time and the like. Ideally, the optimal column length for a given diameter is one that provides efficient separation of impurities from the molecule on a particular resin. Normally, once column height has been determined for a particular purification process, scale up may require increasing the diameter and flow rate proportionately while keeping the height constant.

In general, the amount of purified molecule required will determine the column size. Thus, for example, columns with diameters of up to two or three meters may be used to purify particularly large amounts of material.

The loading solvent may be any solvent but is preferably an aqueous buffer containing the peptide or protein especially during large-scale purification. In some situations, (i.e., purification of GHA) the loading solvent may contain large amounts of polyethylene glycol (about 10–20% w/v).

The flow rate of the column may vary between about 30 cm/hour to about 300 cm/hour. Preferably, the flow rate is about 60 cm/hour when loading the molecule onto the column and about 120 cm/hour when eluting molecule from the column. It should be noted that the flow rate depends on the mobile phase viscosity, bead size, binding efficiency and pressure limits of resin and equipment. The gradient slope is preferably between about 0.1% to about 5% (w/w) diol/ column volumes ("CV"), more preferably between about 1.25% to about 5% (w/w) diol/CV, most preferably about 2.5% (w/w) diol/CV.

In the second step of the current invention, the molecule is eluted from the column with a buffer containing a diol such as 1,5 pentanediol, 1,6 hexane diol or 1,7 heptanediol. Typically, the column will fractionate various components of the mixture during elution. Preferably, the buffer is at a pH of between about 2.0 to about 12.0, more preferably, between about 7.0 and about 11.0 and most preferably between about 6.0 and about 8.0. Those of skill in the art will recognize that a pH of between about 2.0 to about 6.0 is required for acidic chromatography. Similarly, a pH of between about 6.0 to about 8.0 is required for neutral chromatography, while a pH of between about 8.0 to about 12.0 is need for basic chromatography). Any appropriate buffer (e.g., phosphate, acetate, Tris-HCl, triethylamine, trifluoroacetic acid, citrate, etc.) that maintains the pH in the desired range for the purification may be used in practicing the current invention. The selection of a buffer of appropriate concentration is well within the capabilities of those of ordinary skill in the art.

The concentration of diol employed for elution will vary and depends on factors such as the type of molecule being purified, the type of resin utilized, the flow rate and the like. As such, the concentration of diol required to elute a particular molecule from a column may be readily determined by one of skill in the art, without undue experimentation.

The eluting solvent is preferably a terminal alkyl diol, more preferably, 1,5 pentanediol, 1,6 hexanediol or 1,7 heptanediol, most preferably, 1,6 hexanediol. Generally, the maximum percentage of eluting solvent in the buffer is determined by the solubility limit of the molecule and diol together. Preferably, the concentration of 1,6 hexanediol in the buffer is between about 0% and 80%, more preferably, between about 0% to about 50%. Preferably, the concentration of 1,5 pentanediol in the buffer is between about 0% and 80%, more preferably, between about 0% to about 70%. The preferred temperature for elution is generally at about 25° C., although higher or lower temperatures may be employed.

The preferred operating pressures used will vary, depending on whether the column is designed for high pressure or low pressure use. Preferably, high pressure columns will be operated between about 300 psi and about 5,000 psi, more preferably, between about 500 psi and about 2,000 psi. Preferably, low pressure columns will be operated between about 0 psi and about 500 psi, more preferably, between about 0 psi and about 50 psi.

The preferred conditions for GHA purification are packing of between about a 45 cm to about a 200 cm diameter RP-LC column with a methacrylate (e.g., CG71) or styrene based (e.g., CG300) resin using a neutral pH buffer, with a load of between about 1.0 g to about 10 g GHA/liter bed volume. Between about 0% and 50% (v/v) 1,6 hexanediol dissolved in 50 mM Tris HCl is used to elute GHA from the column. The column length is preferably between about 10 cm and about 20 cm. The preferred operating pressure is between about 0 psi and about 500 psi, more preferably, between about 0 psi and about 50 psi.

5.3 PROCESSING OF MOLECULES FOLLOWING PURIFICATION USING UNBRANCHED TERMINAL ALKYLDIOLS

Molecules may be further processed, for example, in order to provide molecules of a higher level of purity. The level of purity required will depend on the potential use of the molecule. In some instances, the method of the current invention, could be the last purification step with molecules needing only buffer exchange or concentration prior to their intended use. In other instances, molecules may need further purification after use of the method of the current invention, prior to their intended use.

Any purification method known to the skilled artisan may be used for further purification, if such is necessary. Such techniques have been extensively described for proteins in "New Protein Techniques: Methods in Molecular Biology," Walker, J. M., ed., Humana Press, Clifton, N.J., 1988; and Protein Purification: Principles and Practice, 3rd. Ed., Scopes, R. K., Springer-Verlag, New York, N.Y., 1987. In general, techniques including, but not limited to, ammonium sulfate precipitation, centrifugation, ion exchange chromatography, affinity chromatography, gel filtration, reverse-phase chromatography (and the HPLC or FPLC forms thereof), recrystallization and adsorption chromatography (i.e., on silica or alumina) may be used to further purify molecules.

EXAMPLES

The following examples are provided to further illustrate the current invention but are not intended to limit the scope of the current invention in any way.

6.1. Example 1

Baker Bond Butyl Experiments

Butyl experiments were performed on an AKTA column (Amersham Pharmacia Biotech, Piscataway, N.J.). Step and linear gradients were run to elute GHA. Gradient length and gradient slopes were adjusted according to the experiment. Effluents were monitored by UV absorbance at 280 nm. The buffer system consisted of 15 mM triethylamine phosphate ("TEAP") at pH 7.2 as buffer A and buffer B was 15 mM TEAP at pH 7.2 containing between 60% and 70% 1,6 hexanediol.

Figure 2:
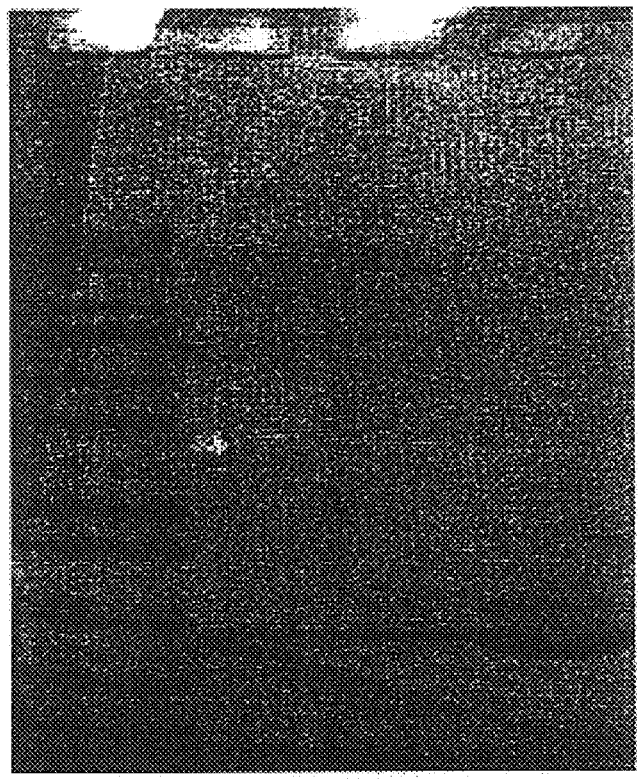
FIG. 2 illustrates SDS-PAGE analysis of the eluate of FIG. 1.
Figure 3:
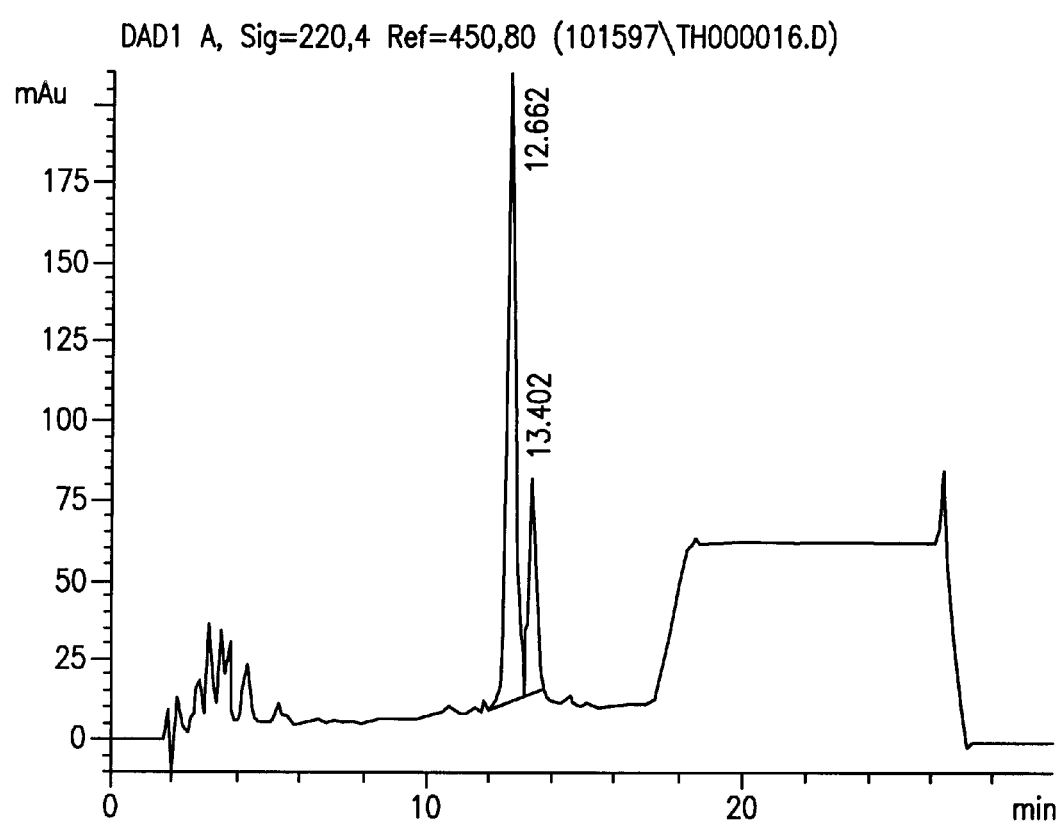
FIG. 3 illustrates C-4 RP-HPLC analysis of the eluate of FIG. 1.

FIG. 1 shows the elution profile of GHA from a widepore butyl column (Mallinckrodt Baker Inc., Phillpsburg, N.J.) using 1,6 hexanediol as an eluant. The SDS-PAGE analysis of the eluant is shown in FIG. 2 (lanes 2–4). Lane 4 which corresponds to fraction 29 clearly contains GHA. Lane 2 and Lane 3 (Fractions 8 and 22, respectively) contain some GHA but to a much lesser extent than Lane 4. Fraction 29 correlates with the apex of the 280 nm absorbance peak. FIG. 3 is the C-4 RP-HPLC analysis of the pooled fractions which shows a GHA peak and a succinylated GHA peak at 12.6 minutes and 13.4 minutes, respectively. The yield of GHA was about 34%.

6.2. Example 2

Small Scale Experiments with Methacrylate Columns CG71-M

A 10 mm×10 cm (8.0 ml) AMBERCHROM (a commercially available resin) CG71-M column (TosoHaas, Montgomeayville, Pa.) was equilibrated at 2 ml/min in 15 mM TEAP, pH 7.2. A 27 ml aliquot of GHA (2.6 mg/ml, dissolved in 50 mM Tris. pH 7.2, 200 mM NaCl) was loaded onto the equilibrated CG71-M column and then washed with equilibration buffer. The column was eluted stepwise with hexanediol beginning with 32.5% hexanediol in 15 mM TEAP, pH 7.2 then with 49% hexanediol in 15 mM TEAP, pH 7.2 and 65% hexanediol in 15 mM TEAP, pH 7.2. The eluant was monitored by absorbance at 280 nm and collected fractions were analyzed by SDS-PAGE and RP-HPLC.

Figure 4:
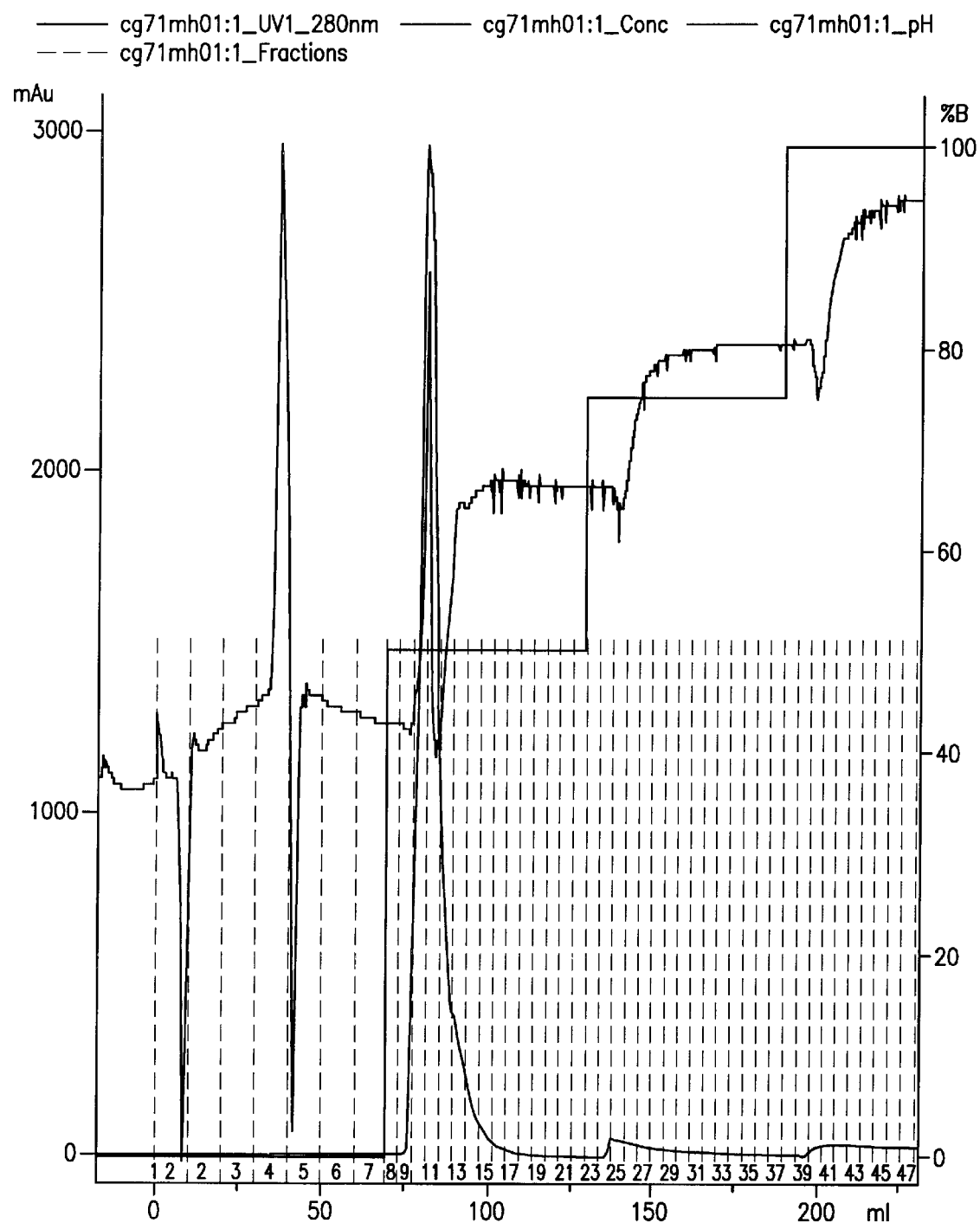
FIG. 4 illustrates the elution profile of GHA from CG71-M RP-LC column using a step gradient of 1,6 hexanediol in 15 mM triethylamine phosphate at pH 7.2.
Figure 5:
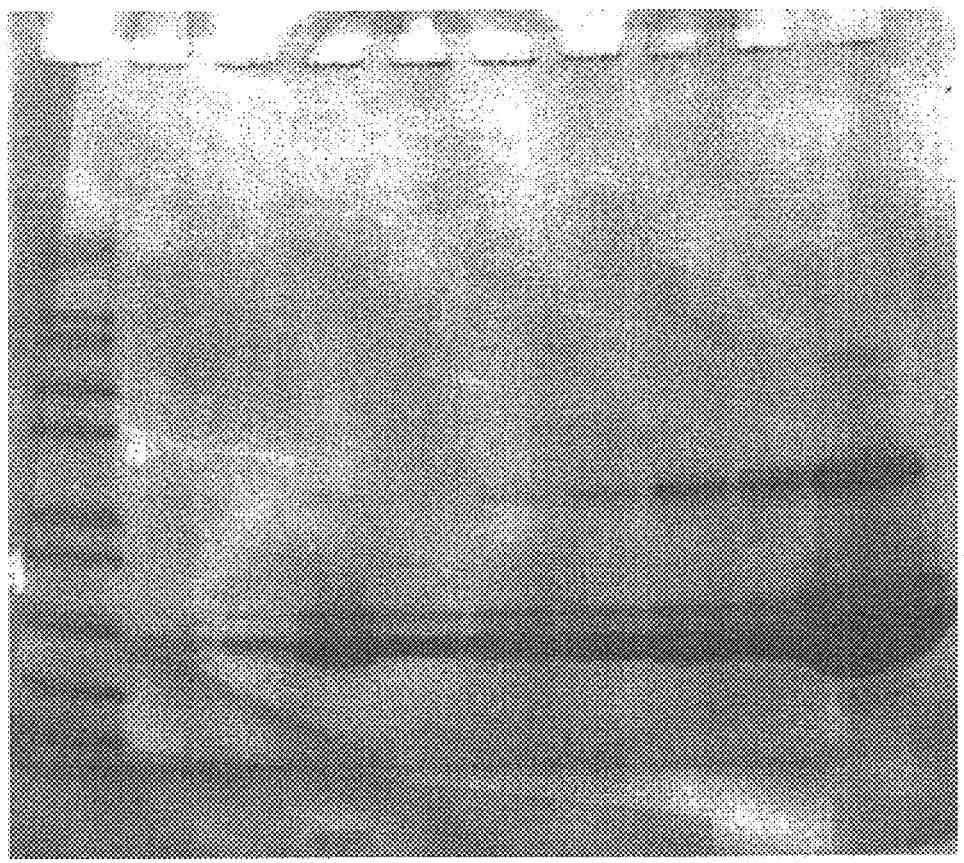
FIG. 5 illustrates SDS-PAGE analysis of the eluate of FIG. 4.
Figure 6:
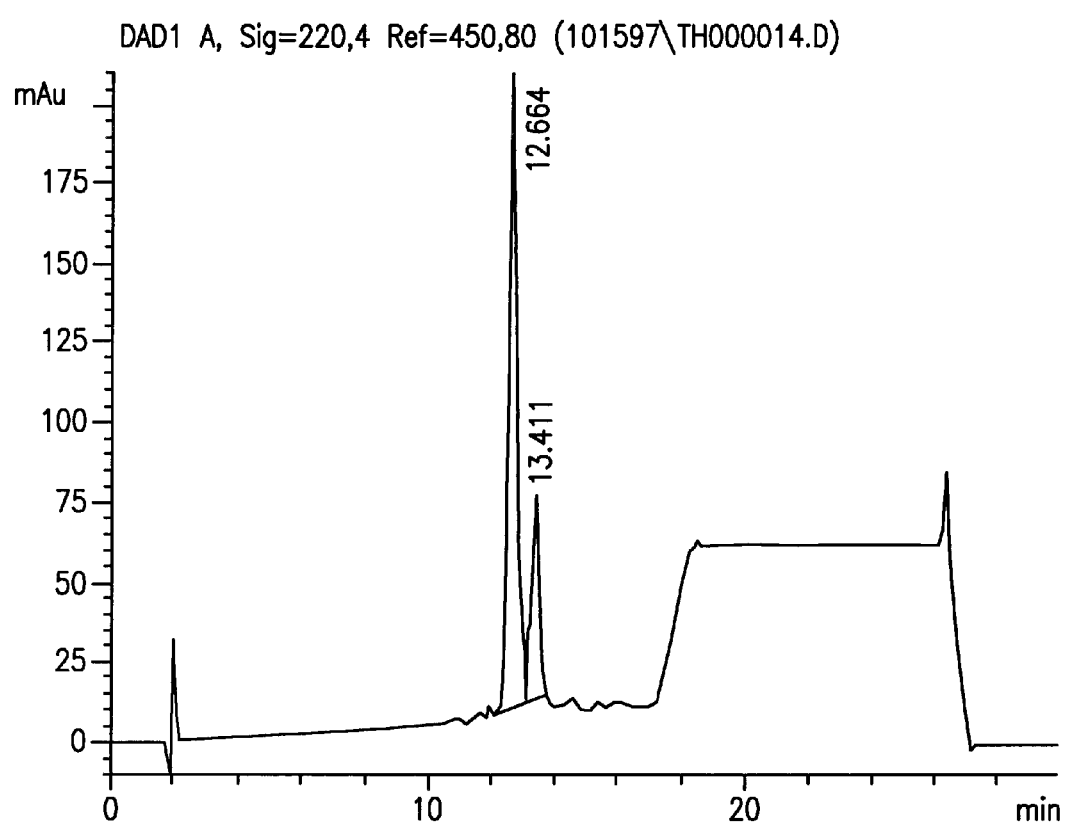
FIG. 6 illustrates C-4 RP-HPLC analysis of the eluate of FIG. 4.

The chromatography results from the 8.0 ml AMBERCHROM (a commercially available resin CG71-M column are shown in FIG. 4. GHA was eluted by a step gradient of 32.5% hexanediol in TEAP, pH 7.2 with a yield of 98%. FIG. 5 shows SDS-PAGE analysis of the eluted protein. As can be seen in FIG. 5, lane 10, the eluted protein consists of primarily GHA along with some contaminmts. Fractions 10 through 14 were pooled and analyzed for protein content by C-4 RP-HPLC, which is shown in FIG. 6. The pool volume was 20 ml at 3.43 mg/ml, which translates to 68.6 mg total GHA. The amount of GHA loaded onto the column was about 69 mg. 6.3. Example 3 pH Experiments with CG71-C

One column (5 mm×10 mm (2.0 ml)) of Amberchrom CG71-C (TosoHaas, Montgomeryville, Pa.) was equilibrated with 15 mM TEAP, pH 7.2, while another column (5 mm×10 mm (2.0 ml)) of Amberchrom CG71-C was equilibrated with 0.1% trifluoroacetic acid ("TFA"). For low pH experiments, buffer A was 0.1% TFA and buffer B was 80% 1,6 hexanediol in 0.1% TFA. For neutral pH experiments, buffer A was 15 mM TEAP, pH 7.2 and buffer B was 15 mM TEAP, pH 7.2, 65% 1,6 hexanediol. Each column was loaded with a total of 15 mg of GHA obtained using the procedure of Hayenga et al., U.S. patent application Ser. No. 09/307,549. Linear gradients of 0% to 100% buffer B were run over 20 column volumes. Effluent was monitored by absorbance at 280 nm. Fractions were collected and analyzed by RP-HPLC and SDS-PAGE.

Figure 7:
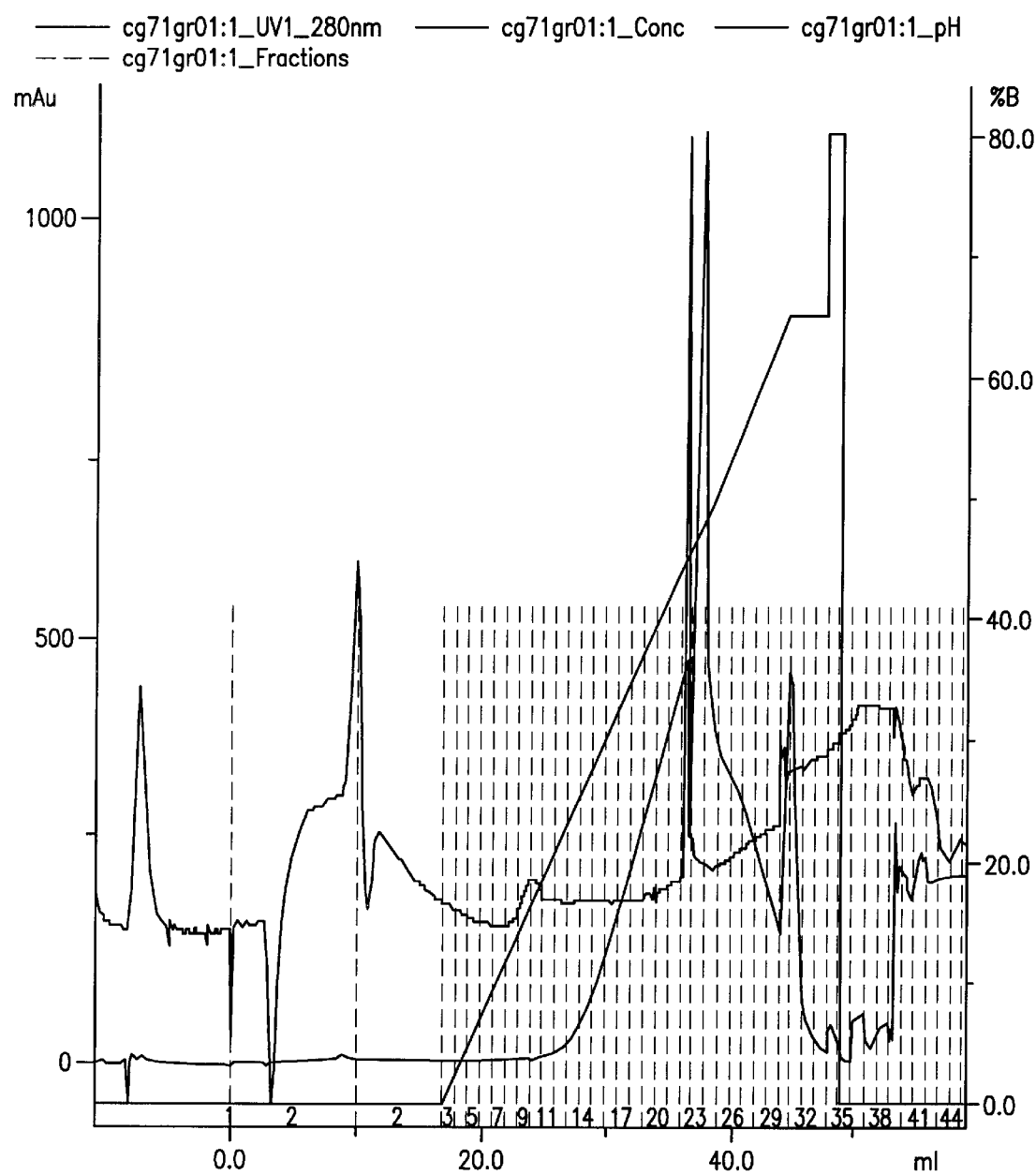
FIG. 7 illustrates the elution profile of GHA from CG71-C RP-LC column using a gradient of 1,6 hexanediol in 15 mM triethylamine phosphate.
Figure 8:
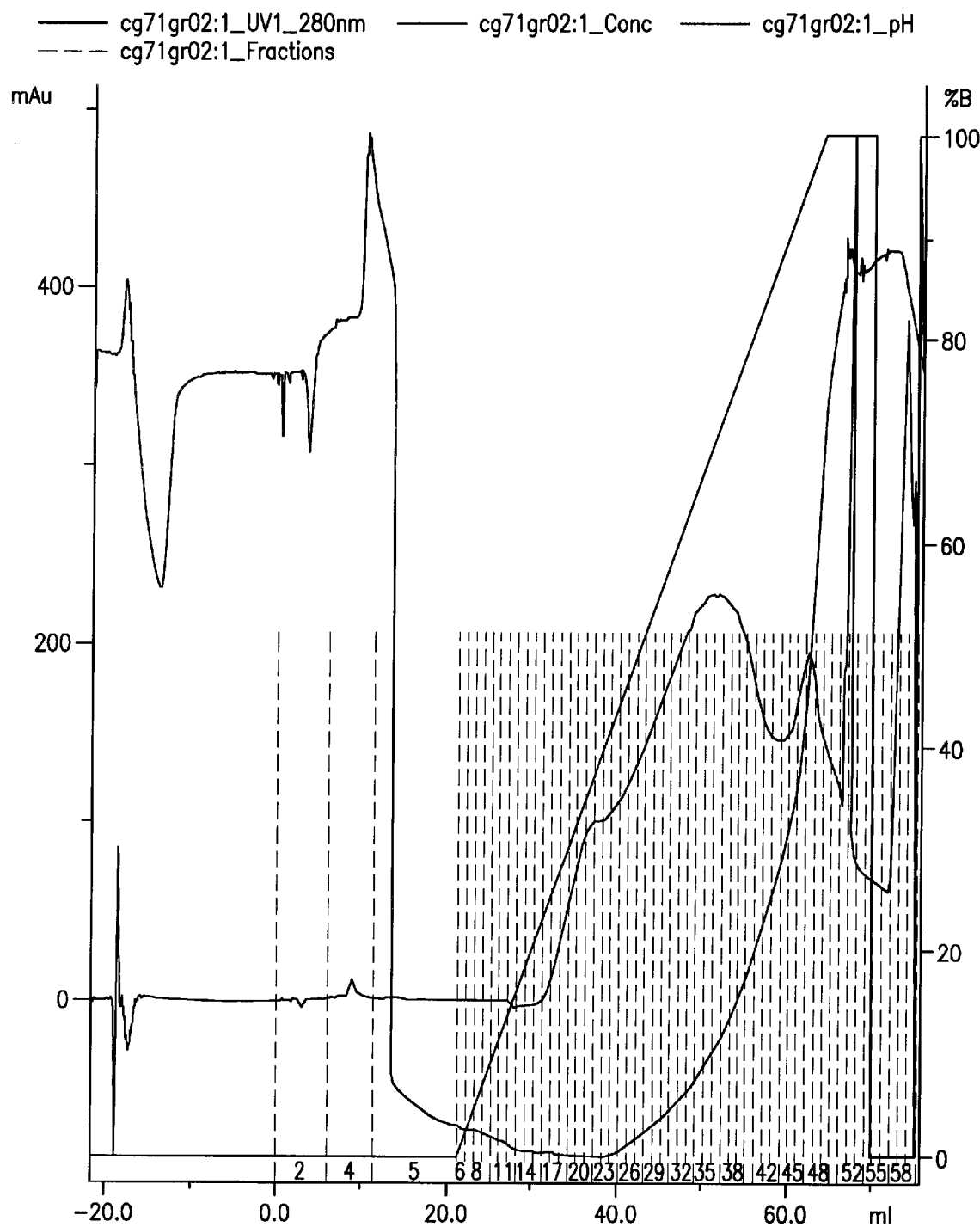
FIG. 8 illustrates the elution profile of GHA from CG71-C RP-LC column using a gradient of 1,6 hexanediol in 0.1% trifluoroacetic acid.
Figure 9:
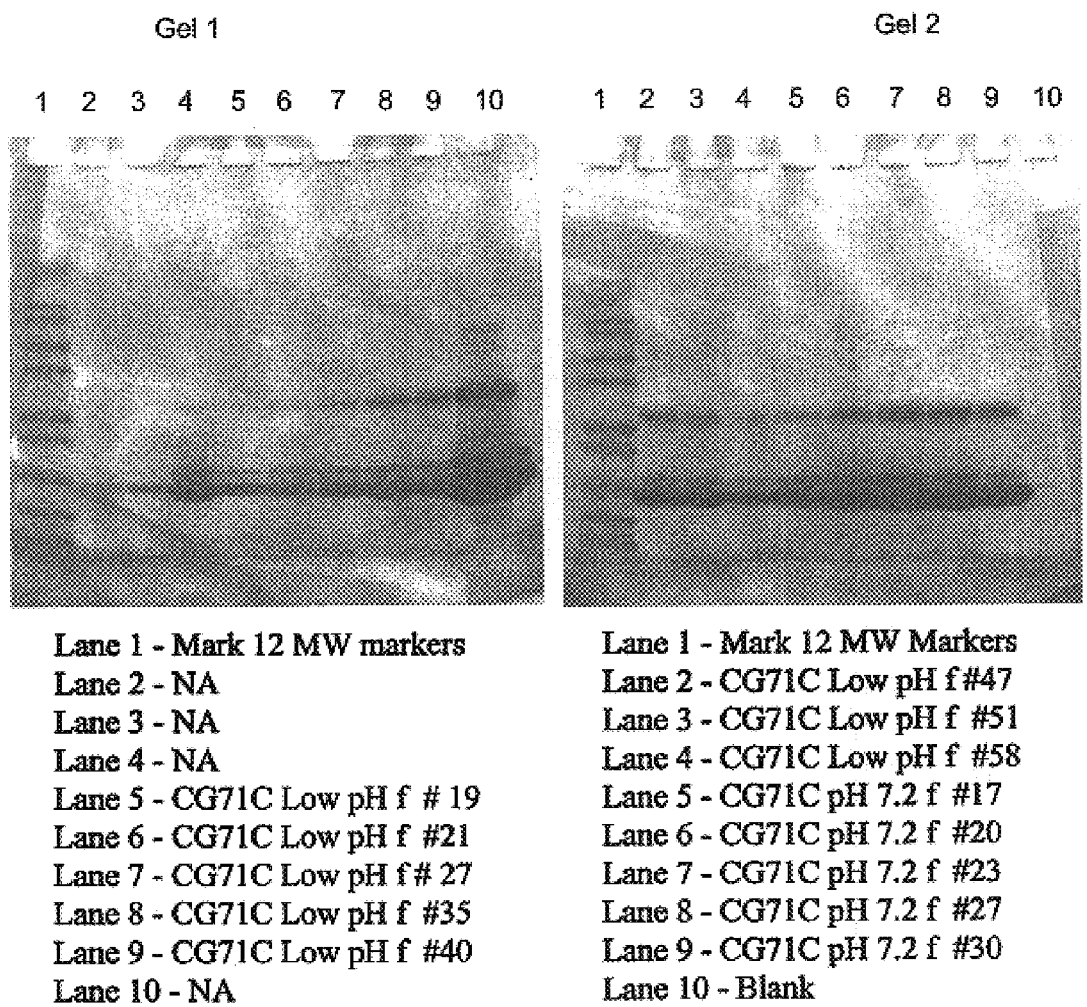
FIG. 9 illustrates SDS-PAGE analysis of the eluate of FIGS. 7 and 8.

The results are shown in FIGS. 7 and FIG. 8, which demonstrate that 1,6 hexanediol can elute GHA from methacrylate based columns. Fractionation of other proteins or closely related contaminants is evident in the elution profiles since the peaks in the elution profile have shoulders. The elution profile of the neutral pH experiments is spread over a smaller volume then the elution profile at low pH. SDS-PAGE analysis of the low pH experiment (FIG. 9, gel 1, lanes 5–9 and gel 2, lanes 2–4) and the neutral pH experiment (FIG. 9, gel 2, lanes 5–9) indicates that the fractions contain GHA, which was confirmed by C-4 RP-HPLC analysis. The pooled fraction volumes were 15 ml and 33 ml for the pH 7.2 experiment and the low pH experiment, respectively. The yield for each column is in excess of 96%, indicating recovery of about 14.5 mg of GHA.

6.4. Example 4

Screening Methacrylate Resins (CG71-M and CG71-C) and Styrene Divinylbenzene Resin (CG300-M)

Three columns containing AMBERCHROM (a commercially available resin) CG71-M (TosoHaas, Montgomeryvilie, Pa.), AMBERCHROM (a commercially available resin) CG71-C and AMBERCHROM (a commercially available resin) CG300-M resin, (TosoHaas, Montgomeryville, Pa.) respectively were equilibrated in 15 mM TEAP, pH 7.2. Each column was loaded with 40 ml of diluted top phase material (prepared by two-phase extraction, using the procedure of Hayenga at al., U.S. patent application Ser. No. 09/307,549) which contained about 0.5 mg/ml GHA. The columns were loaded at 10 mg/ml. After loading, each column was washed with 15 mM TEAP, pH 72. was used to elute GHA from the columns (about 20 column volumes of solvent were used). Effluent was monitored by absorbance at 280 nm and appropriate fractious were collected. Fractions were analyzed by C-4 RP-HPLC and SDS-PAGE.

It was decided to use the method of the present invention as a replacement for a AMBERCHROM (a commercially available resin) CG1000 column, which is a styrene divinylbenzene based reverse phase resin that was previously used to purify GHA from diluted top phase obtained using the procedure of Hayenga et al., U.S. patent application Ser. No. 09/307,549. Acetonitrile was typically used to elute GHA from AMBERCHROM (a commercially available resin) CG1000 column, which significantly increased cost associated with the process because of handling requirements and expensive disposal.

Figure 10:
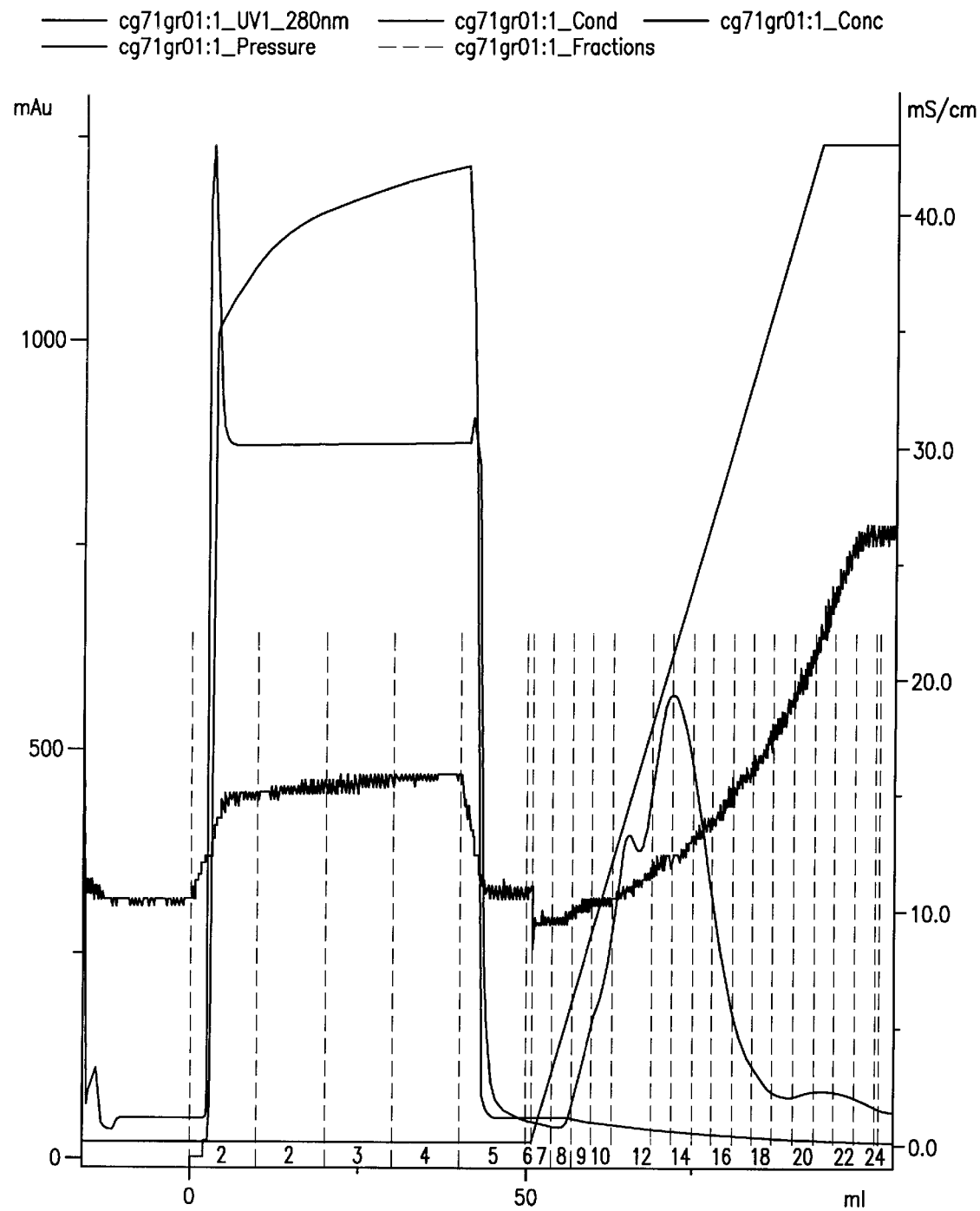
FIG. 10 illustrates the elution profile of GHA from a CG71-C column using a gradient of 0% to 65% 1,6 hexanediol in 15 mM triethylamine phosphate, pH 7.2.
Figure 11:
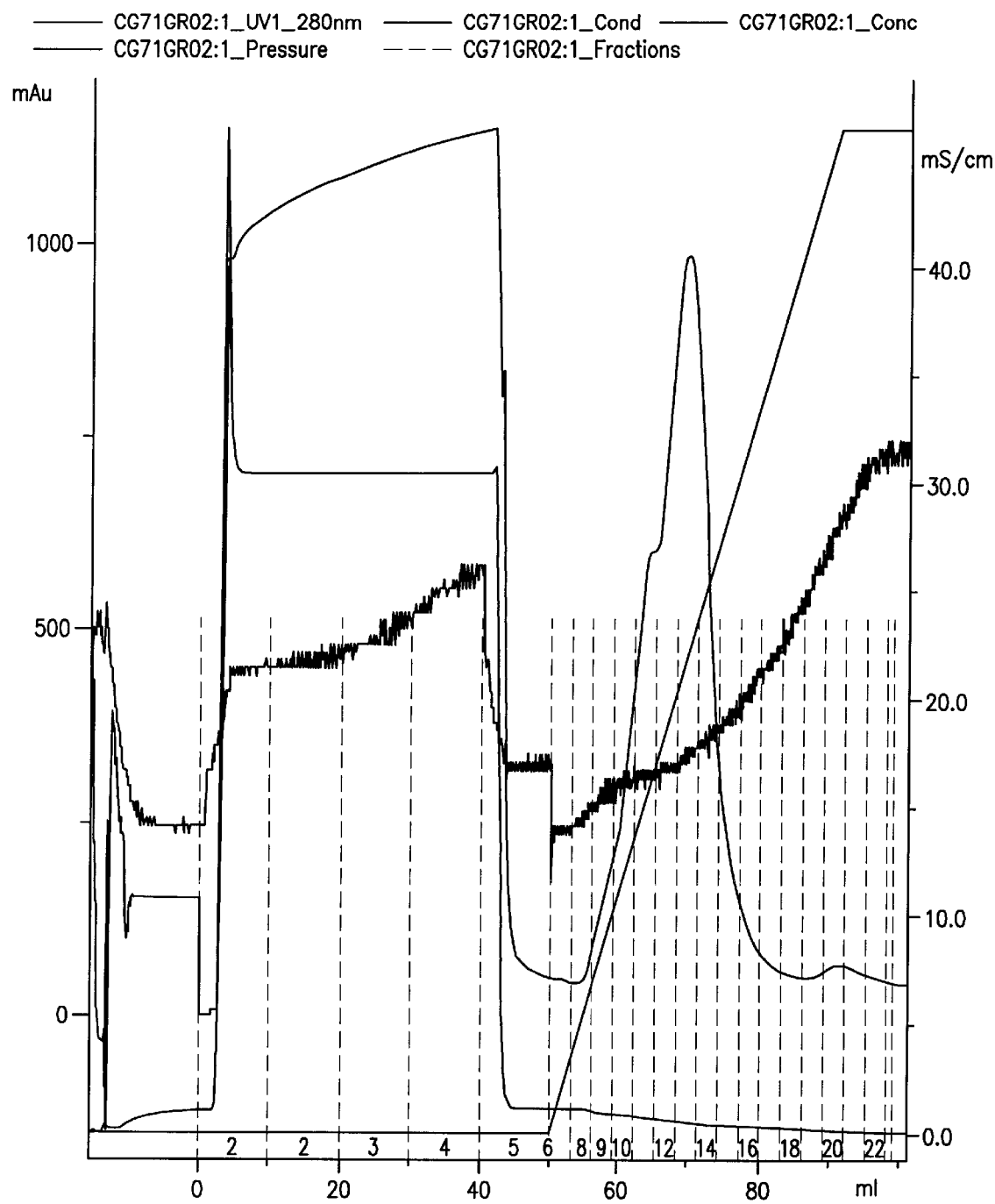
FIG. 11 illustrates the elution profile of GHA from a CG71-M column using a gradient of 0% to 65% 1,6 hexanediol in 15 mM triethylamine phosphate, pH 7.2.
Figure 12:
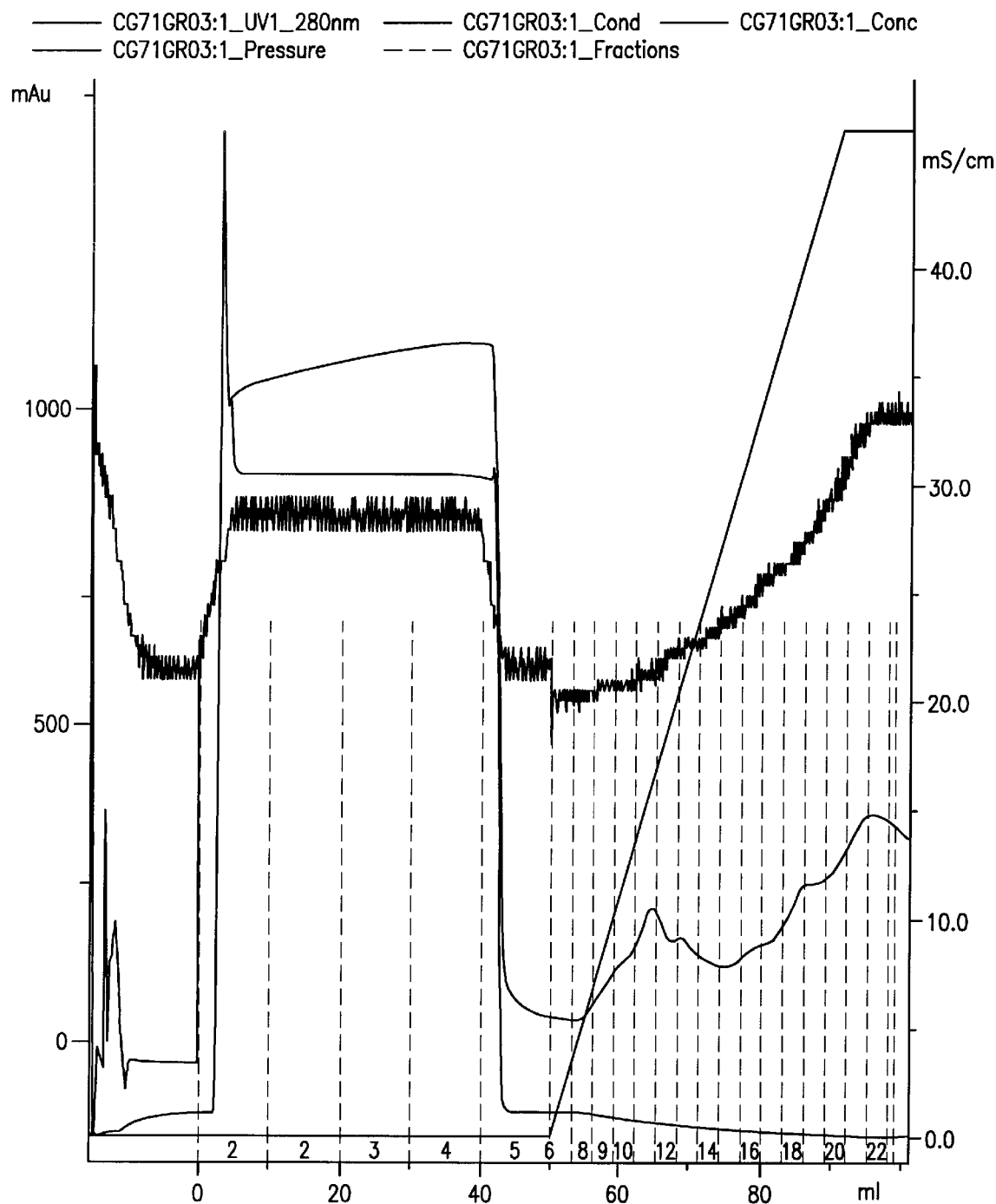
FIG. 12 illustrates the elution profile of GHA from a CG300-M column using a gradient of 0% to 65% 1,6 hexanediol in 15 mM triethylamine phosphate, pH 7.2.
Figure 15:
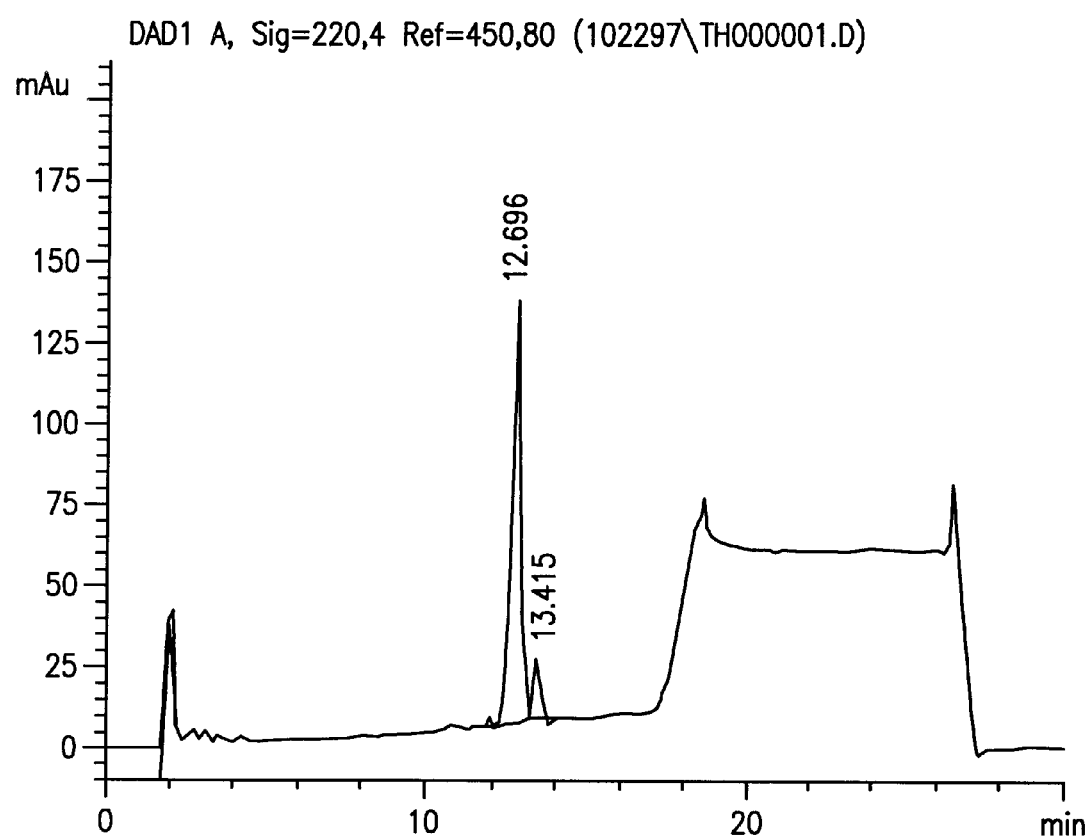
FIG. 15 illustrates the C-4 RP-HPLC analysis of the eluate of FIG. 10.
Figure 16:
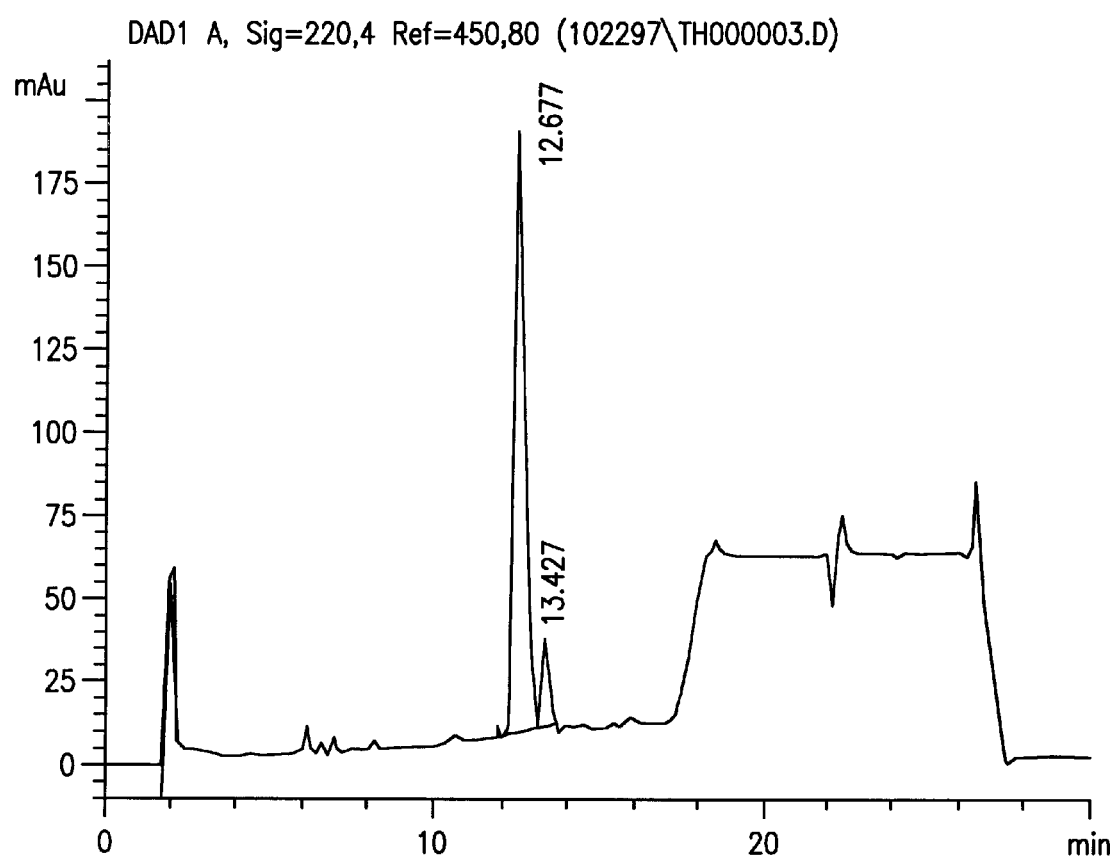
FIG. 16 illustrates the C-4 RP-HPLC analysis of the eluate of FIG. 11.

Thus, AMBERCHROM (a commercially available resin) CG71-C, AMBERCHROM (a commercially available resin) CG71-M methacrylate resins and AMBERCHROM (a commercially available resin) CG300-M styrene divinylbenzene resin loaded as described above were eluted using a 1, 6 hexanediol gradient specified above. FIGS. 10, 11 and 12 show the elution profiles generated on each resin, respectively. Each chromatogram illustrates that 1, 6 hexanediol can elute protein from each resin. FIG. 13 illustrates SPS-PAGE analysis for CG71C and CG71M elution pools, while FIGS. 15 and 16 are C-4 RP-HPLC chromatograms for CG71C and CG71M elution pools, respectively.

Fractions 11 through 18 (24 ml) comprised the pooled fractions for the AMBERCHROM (a commercially available resin) CG71-C experiment (84% yield of GHA). The remaining material was found in the void volume, which suggests that the binding capacity of this resin for is about 8 mg/ml of GHA. Fractions 10 through 16 (21 ml) were pooled for the AMBERCHROM (a commercially available resin) CG71-M experiment (103% yield of GHA). The loading for this column, based upon GHA, is 10 mg/ml. No GHA was detected in the AMBERCHROM (a commercially available resin) CG71-M void volume. The data is summarized in Table 1, shown below.

TABLE 1

| Sample | Pool Concentration (mg/ml) | Volume of Pool (ml) | Total GHA in Pool (mg) | Total GHA loaded (mg) | Yield (%) |
|---|---|---|---|---|---|
| CG71-C | 0.715 | 24 | 17.2 | 20.4 | 84 |
| CG71C flow through fraction | 0.082 | 50 | 4.1 | 20.4 | 20 |
| CG71M | 1.005 | 21 | 21.1 | 20.4 | 103 |
| CG71M flow through fraction | 0 | NA | 0 | 20.4 | 0 |

Figure 14:
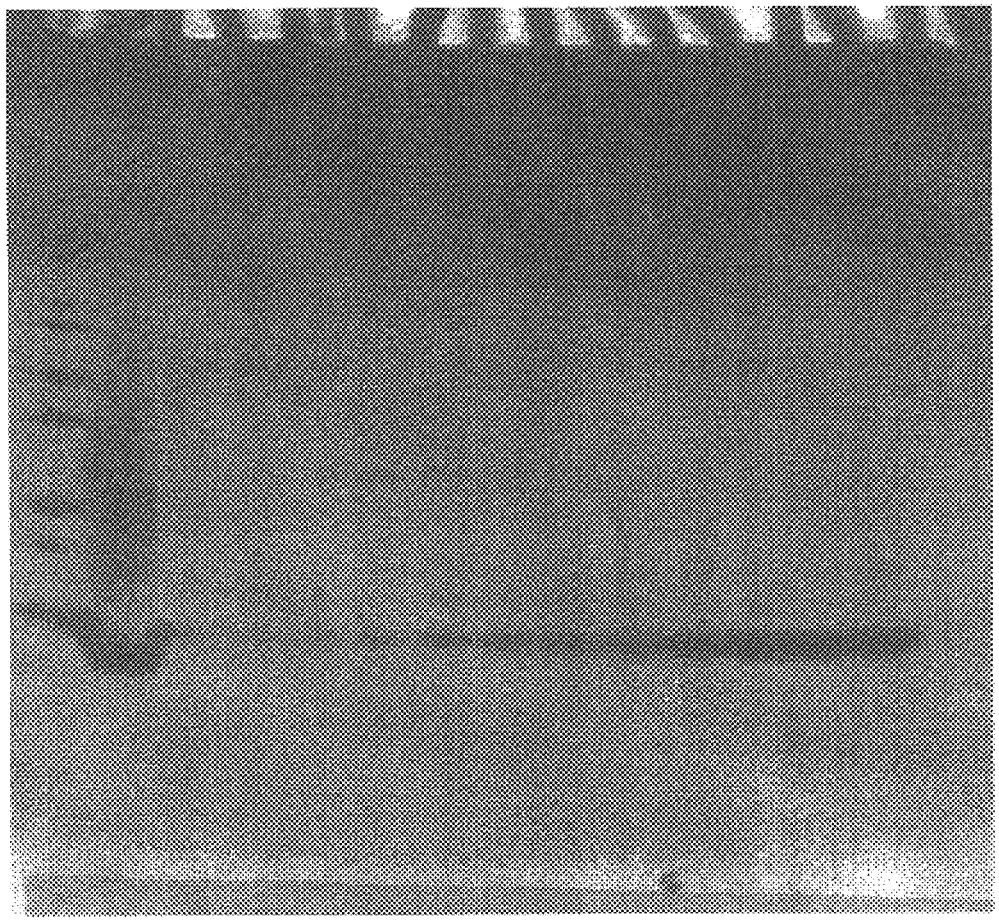
FIG. 14 illustrates SDS-PAGE analysis of the eluate of FIG. 12.
Figure 17:
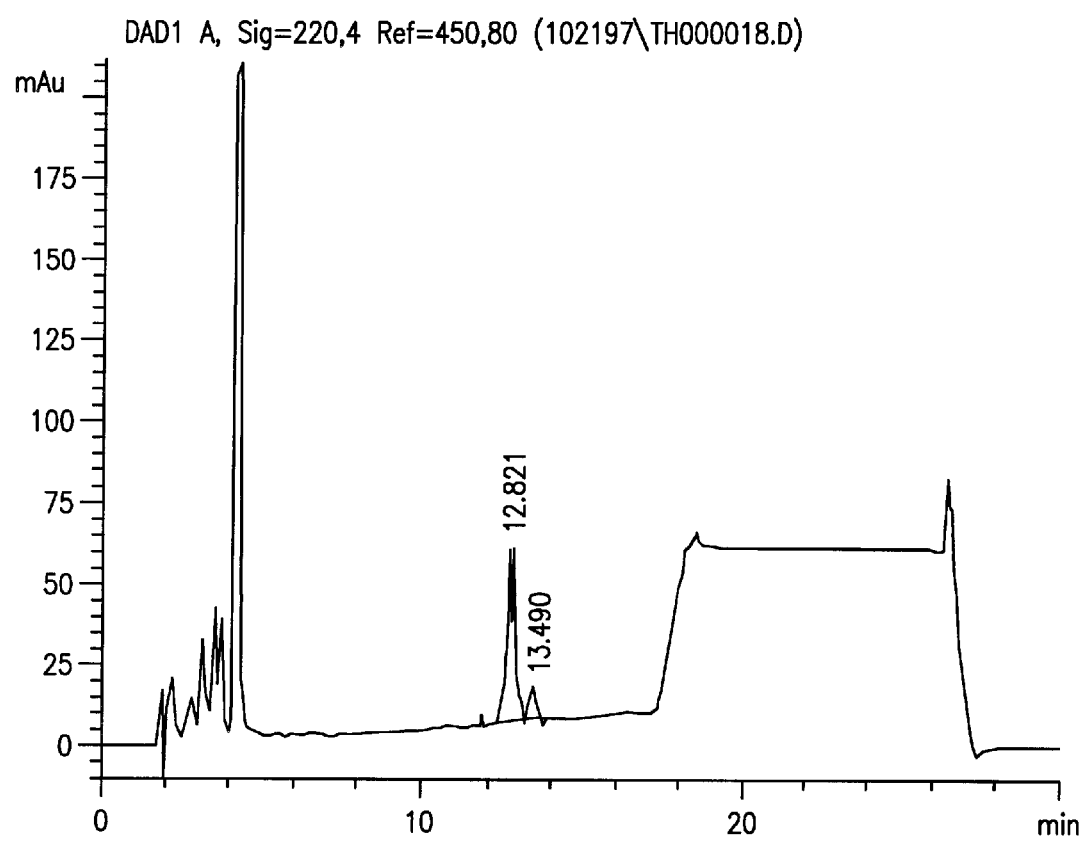
FIG. 17 illustrates the C-4 RP-HPLC analysis of the eluate of FIG. 12.

The AMBERCHROM (a commercially available resin) CG3000-M experiment and the resulting C-4 RP-HPLC and SDS-PAGE analysis (FIGS. 17 and 14, respectively) shows that some GHA is eluted from this column by 1,6 hexanediol. However, the profile (FIG. 11) shows that elution is diffuse and trials beyond the end of the gradient. Thus, under these conditions, 50% 1,6 hexanediol fails to completely elute GHA from the resin.

6.5. Example 5

Scale up using Step Gradient

Since AMBERCHROM (a commercially available resin) CG71-M resin provided favorable results in the preliminary experiments described in Example 4, this resin warn selected for the scale-up experiment. A 235 ml (5 cm×12 cm) AMBERCHROM (a commercially available resin) CG71-M column was poured and equilibrated in 50 mM Tris HCl. pH 7.2. Four liters of 2× diluted top phase, obtained by the procedure of Hayenga et al., U.S. patent application Ser. No. 09/307,549, was loaded on the column at 20 ml/min and eluted with a step gradient of 50% 1,6 hexanediol in 50 mM Tris HCl, pH 7.2. The Column was monitored by absorbance a 280 nm and fractions were collected and analyzed by C-4 RP-HPLC and SDS-PAGE.

Figure 18:
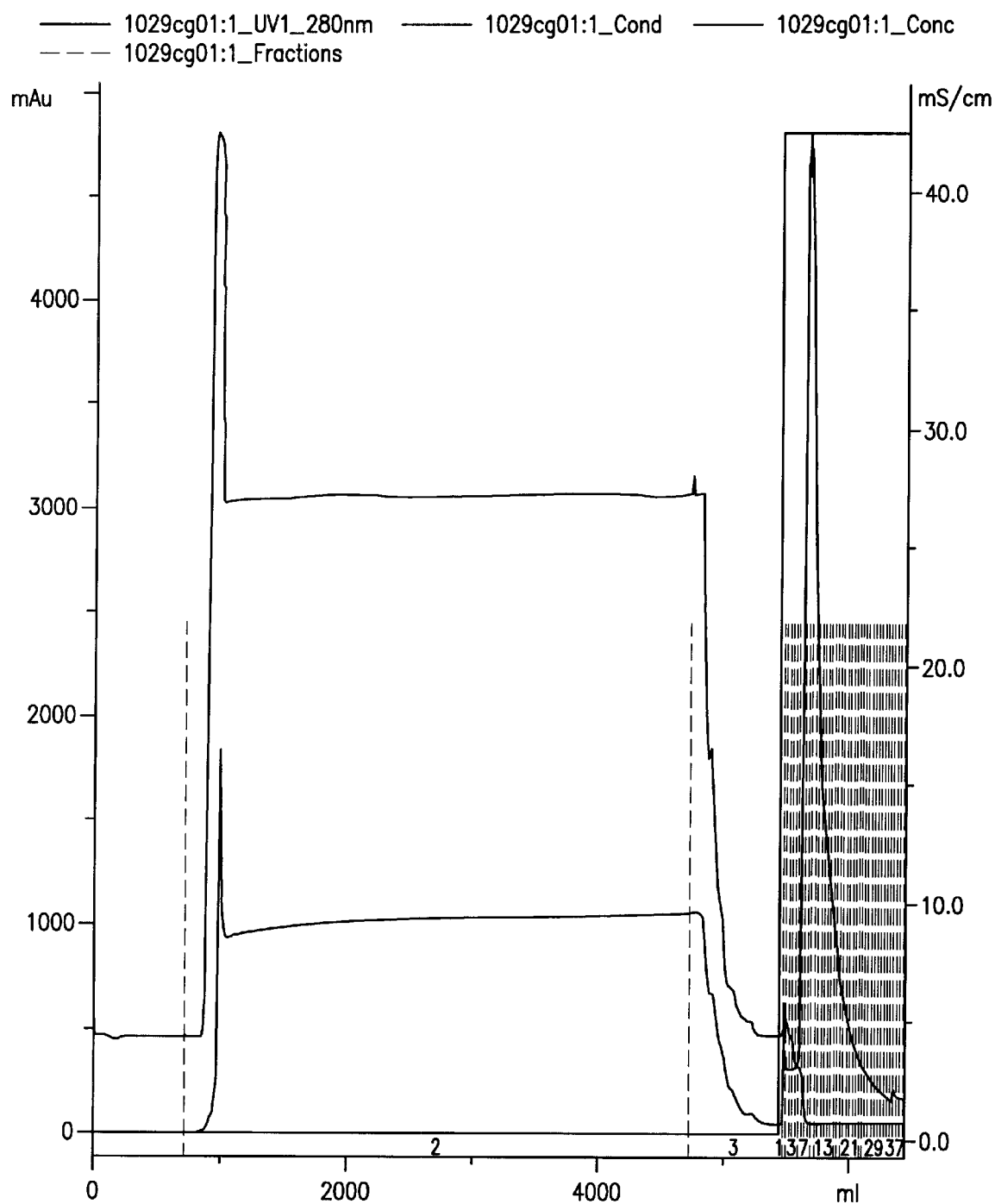
FIG. 18 illustrates the elution profile of GHA from a 240 mL CG71-M column using a step gradient of 50% 1,6 hexanediol in 15 mM triethylamine phosphate, pH 7.2.
Figure 19A:
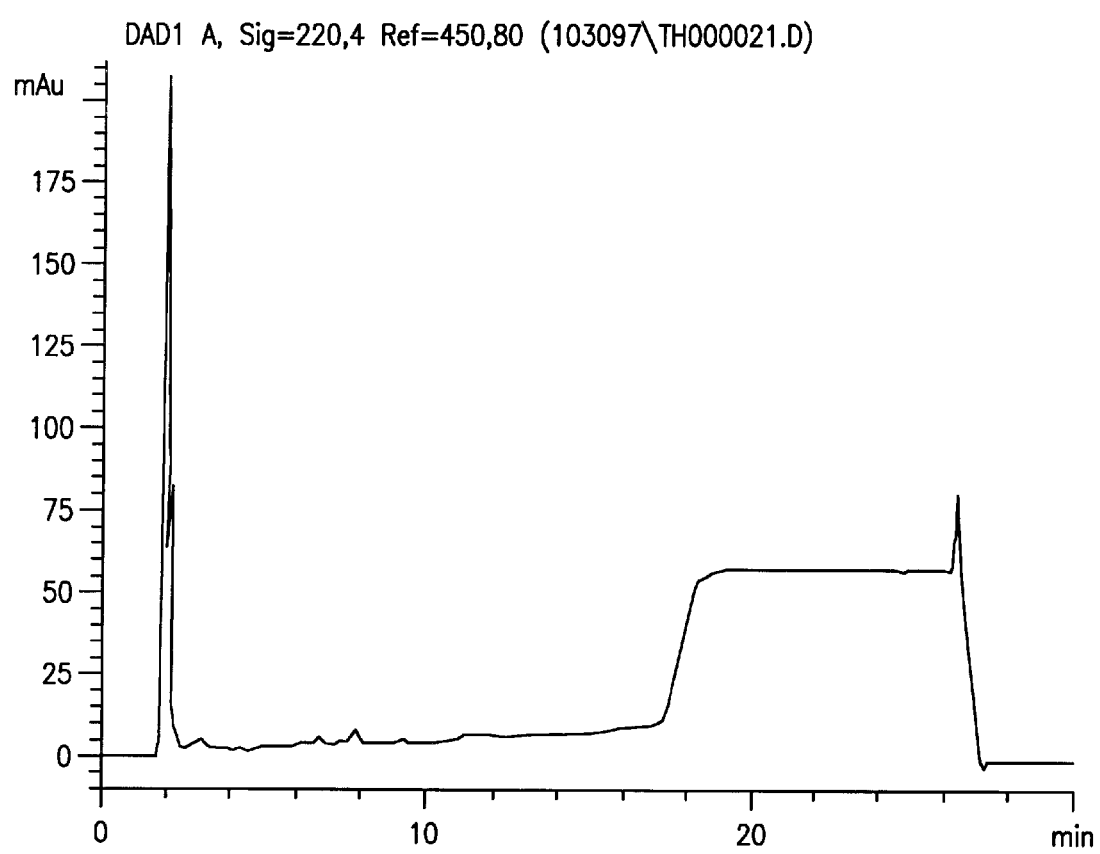
FIG. 19(a) illustrates the C-4 RP-HPLC analysis of the flow through from the column of FIG. 18.
Figure 19B:
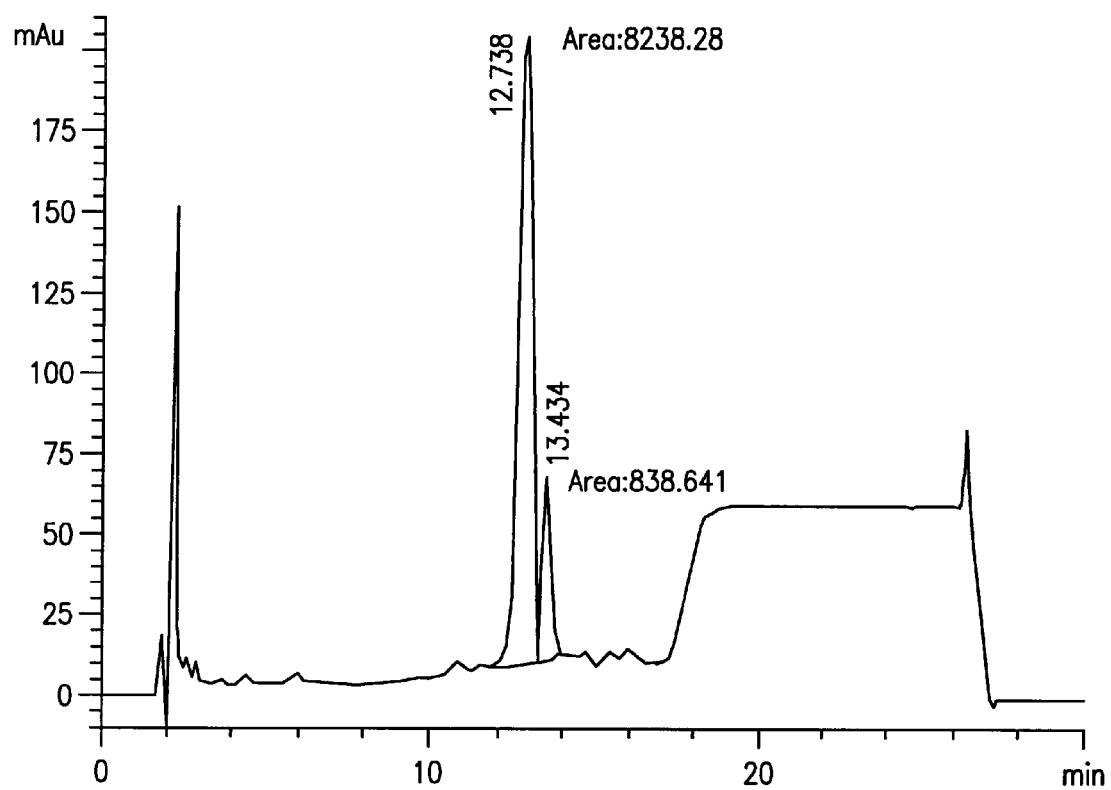
FIG. 19(b) illustrates the C-4 RP-HPLC analysis of the eluate of FIG. 18.

The chromatogram for the 235 ml AMBERCHROM (a commercially available resin) CG71-M experiment is shown in FIG. 18. The elution profile shows one peak, which is consistent with a step elution at 50% 1, 6 hexanediol. The column load for this experiment was 8.3 mg/ml (about 2000 mg on 235 ml of resin). The C-4 RP-HOLC Chromatogram (FIG. 19a) for the void volume shows no GHA. However, the yield of GHA was only 67%. Fractions 6–12 constitute the main peak, which accounts for 47% of the material eluted. Fractions 1 to 5 and 13 to 20 make up the balance. The C-4 RP-HPLC chromatogram (FIG. 19b) for the pooled fractions showed essentially pure GHA. Later experiments demonstrated that a linear gradient from 0% to 50% 1,6 hexanediol in 50 mM Tris HCl, pH 7.2 provided superior yields of GHA, which were generally between 80 and 95%.

6.6. Example 6

Large Scale Manufacturing of GHA

A 100 L (100 cm×12 cm) AMBERCHROM (a commercially available resin) CG71-M column was equilibrated with 3 column volumes of 50 mM TRIS, pH 7.2, at 150 cm/hr. Diluted top phase (about 1000 L) containing GHA, obtained from the procedure Hayenga et al., U.S. patent application Ser. No. 09/307,549 was loaded onto the column at 7.9 L/min. About 10 g of GHA per L of resin was loaded on the column. The column was then washed with 2 column volumes of 50 mM Tris, pH 7.2 at 60 cm/hr and 3 column volumes of 50 mM Tris, pH 7.2 at 120 cm/hr. GHA was eluted with a 20 column volume gradient from 0 to 50% 1,6 hexanediol. Buffer A is 50 mM Tris, pH 7.2 (10 column volumes) and buffer B is 50% (w/w) 1, 6 hexanediol, 50 mM Tris, pH 7.2 (10 column volumes). Elution of GHA was monitored by absorbance at 280 nm.

Figure 20:
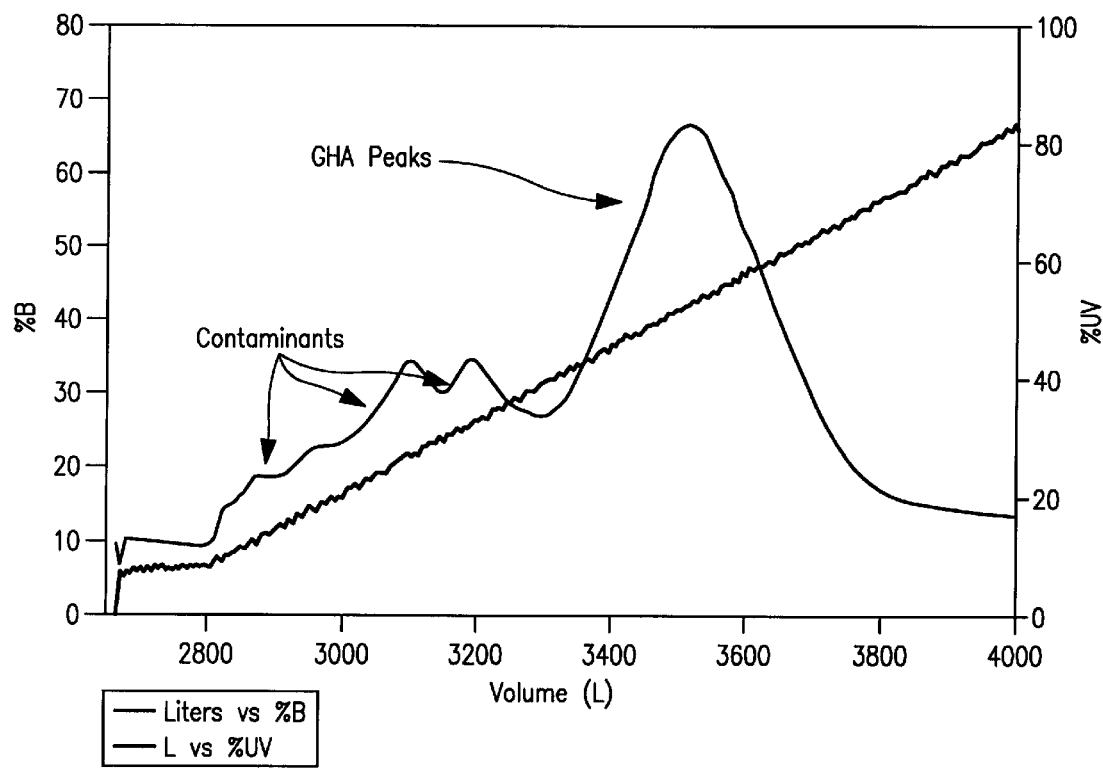
FIG. 20 illustrates the elution profile of GHA from a 100 L CG71-M column using a gradient of 0% to 50% 1,6 hexanediol in 15 mM triethylamine phosphate, pH 7.2.

Two major peaks eluted during the gradient and were collected separately. In general, the first peak elutes during the second and third column volumes. The main peak, which contains GHA, elutes between the sixth and twelfth column volumes (approximately, six column volumes) and when pooled is about 600 L. Both peaks were analyzed by C-4-RP-HPLC to determine the GHA concentration. Generally, the yield of GHA was between about 80% and about 95% in the main peak. FIG. 20 shows a typical chromatogram for a 100 L scale purification using CG71-M resin, while Table 2, below, shows the yields for five different GHA purifications using the same resin.

TABLE 2

| Run # | Concentration of GHA pool (g/L) | Volume of Pool (L) | Total GHA eluted in pool (g) | GHA loaded onto CG71-M (g) | Yield (%) |
|---|---|---|---|---|---|
| 1 | 1.65 | 738 | 1223 | 819 | 149 |
| 2 | 0.94 | 716 | 679 | 794 | 86 |
| 3 | 1.26 | 704 | 891 | 1087 | 82 |
| 4 | 1.18 | 739 | 874 | 1037 | 84 |
| 5 | 0.23 | 590 | 136 | 128 | 106 |

The column was regenerated after each purification with 2 column volumes of a 0–100% isopropanol gradient, 1 column volume of isopropanol, a 100–0% reverse isopropanol reverse gradient followed by 1 column volume of water and 1.5 column volumes of 0.5 N sodium hydroxide. The column was contacted with 0.5N NaOH for between about 12 to about 18 hours. Then the column was washed with 2 column volumes of distilled water. The column may be stored in 20% ethanol and 0.01 N NaOH.

6.7 Example 7

Experiments with Other Proteins and Peptides

Five different proteins or peptides were selected to determine the general applicability of the method. Synthetic met-enkephalin (Tyr-Gly-Gly-Phe-Met, Bachem Biosciences Inc (Philadelphia, Pa.), 0.5 mg/ml), synthetic α-MSH (acetyl-ACTH, Bachem Biosciences Inc (Philadelphia, Pa.), 0.5 mg/ml), synthetic somatotropin (Bachem Biosciences Inc (Philadelphia, Pa.), 0.5 mg/ml), somatostatin (isolated from porcine pituitaries (0.5 mg/ml)) and recombinant hGH (Bachem Biosciences Inc (Philadelphia, Pa.) 0.5 mg/ml) were individually loaded onto a 1 ml (5 mm×5 cm) Amberchrom CG71-M column at about 1 mg/ml of resin. An AKTA system (i.e., a FPLC system from Amersham Pharmacia Biotech, Piscataway, N.J.) was set up with buffer A as 50 mM Tris HCl, pH 7.5 and buffer B as 50% 1,6 hexanediol, 50 mM Tris HCl, pH 7.5. A linear gradient of 0 to 100% buffer B over 20 CV was run to elute each column. Fractions were collected and analyzed by C-4 HPLC and SDS-PAGE.

Figure 21:
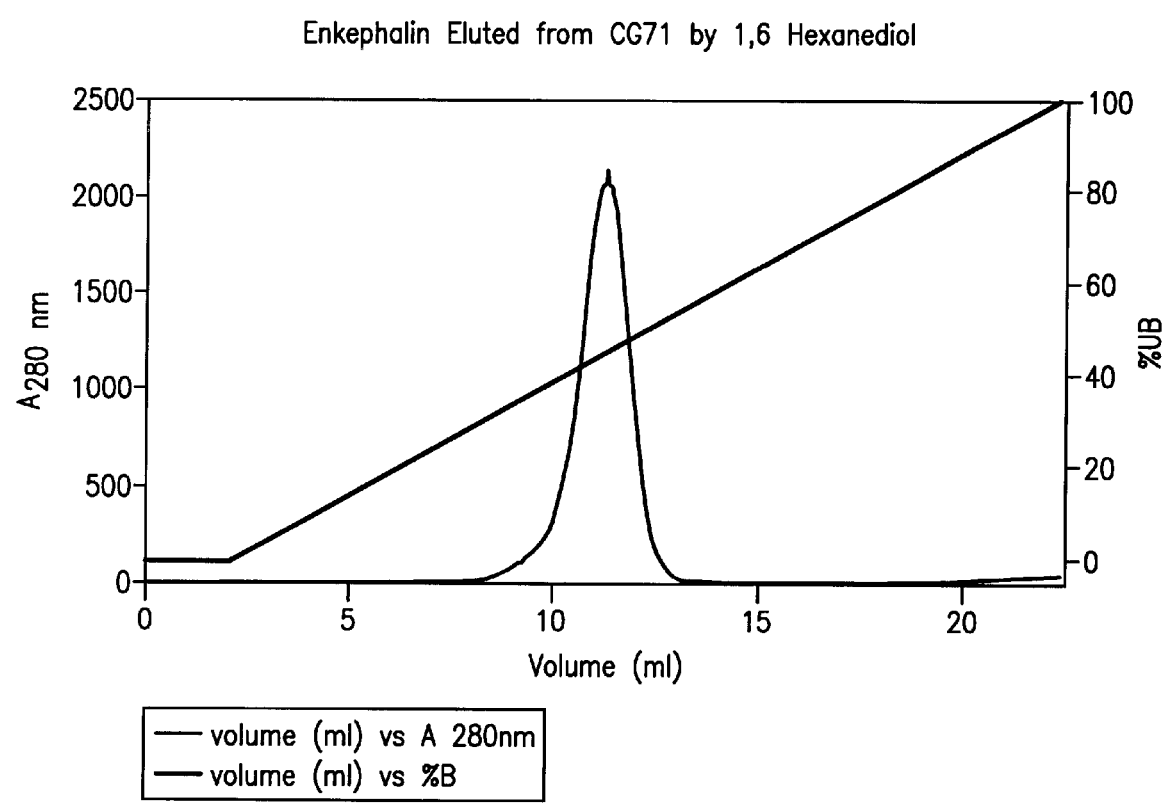
FIG. 21 illustrates the elution profile of enkephalin from a CG71-M column using a gradient of 0% to 50% 1,6 hexanediol in 50 mM Tris, pH 7.5.

FIG. 21 is the elution profile for enkephalin eluted from CG71-M with a gradient of 1,6 hexanediol. Enkephalin elutes when the solvent at the inlet of the column is approximately 31% B.

Figure 22:
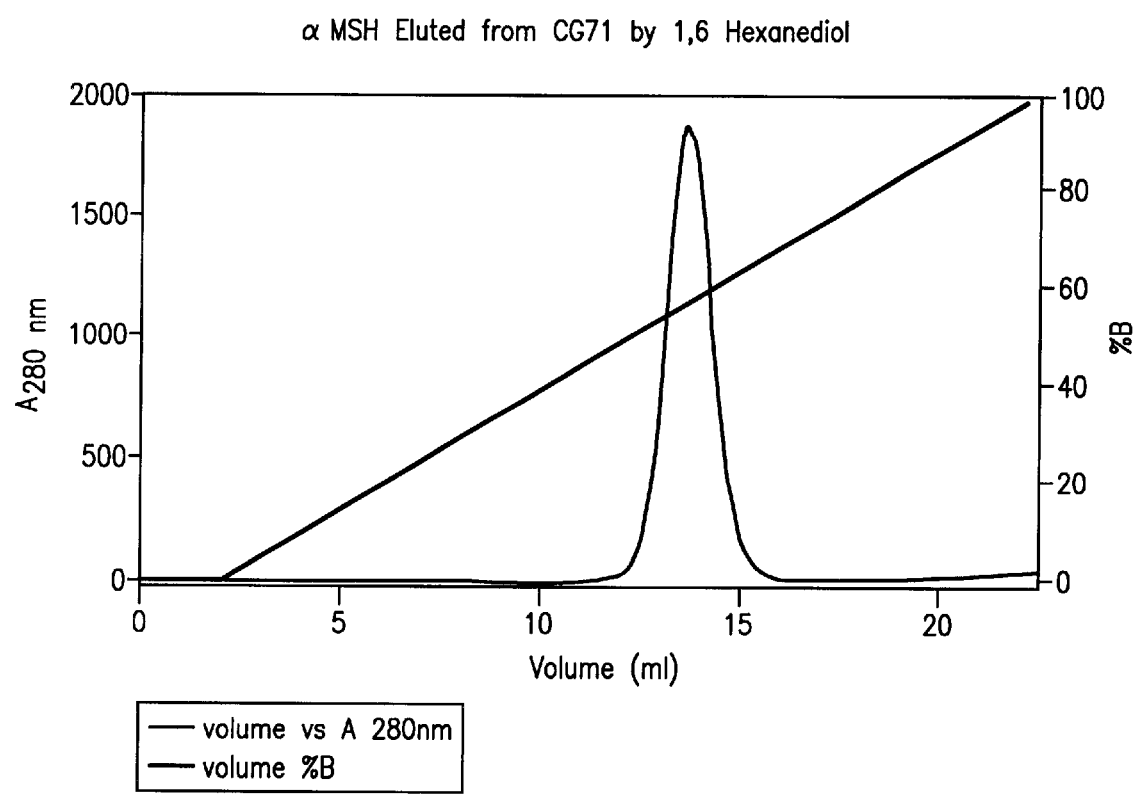
FIG. 22 illustrates the elution profile of A-MSH from a CG71-M column using a gradient of 0% to 50% 1,6 hexanediol in 50 mM Tris, pH 7.5.
Figure 23A:
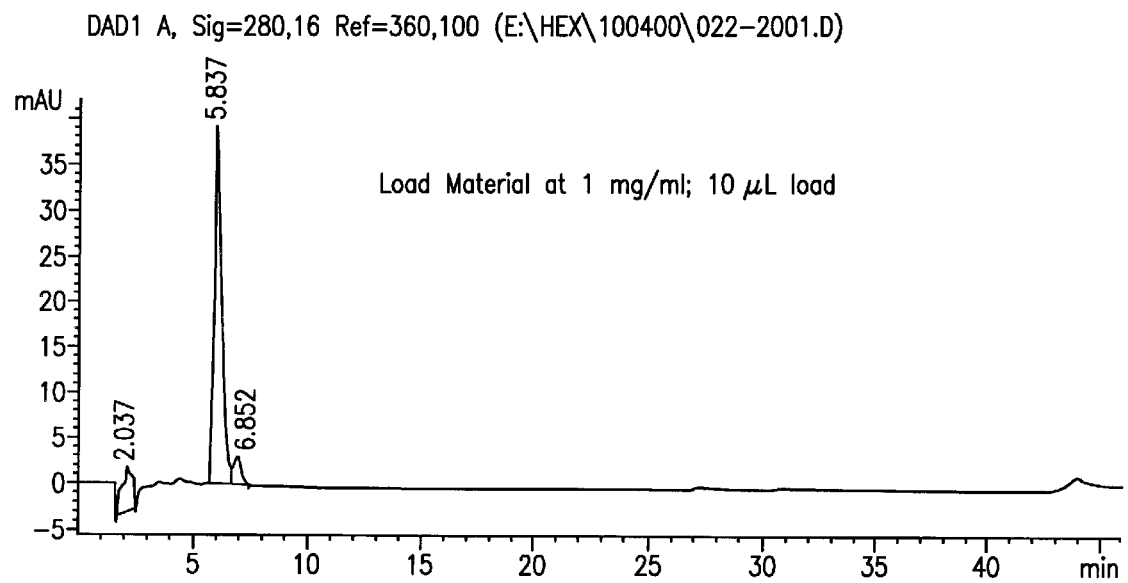
FIG. 23(a) illustrates the C-4 RP-HPLC analysis of a 1.0 mg/mL solution of α-MSH.
Figure 23B:
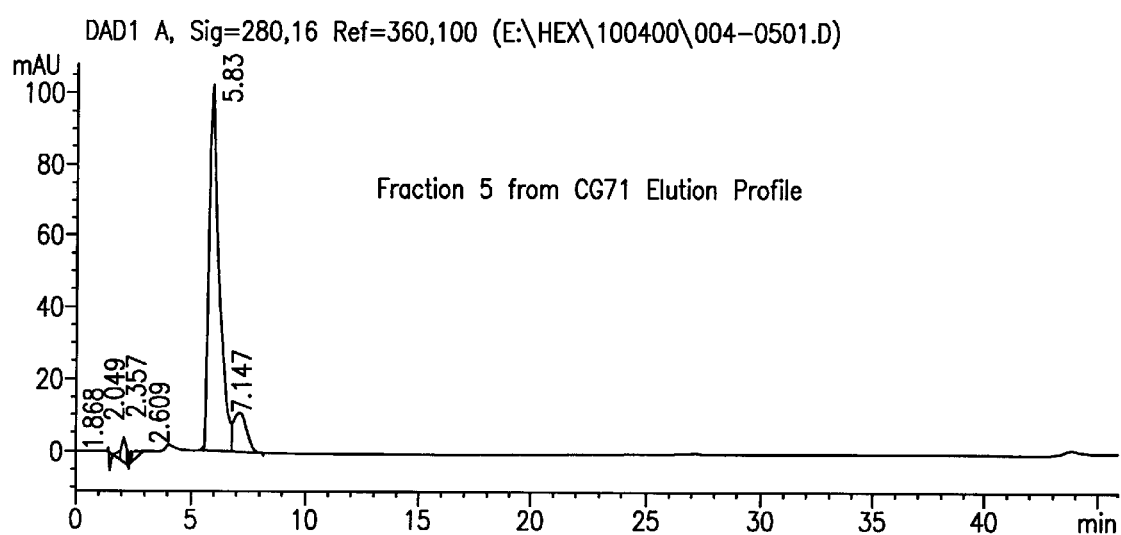
FIG. 23(b) illustrates the C-4 RP-HPLC analysis of the eluate of FIG. 22.

The chromatogram depicting the elution of α-MSH is seen in FIG. 22. The protein elutes when the solvent at the inlet of the column is approximately 54% buffer B. FIG. 23(a) shows a control, while FIG. 23(b) shows the C-4 RP-HPLC analysis results of the CG-71 eluate.

Figure 24:
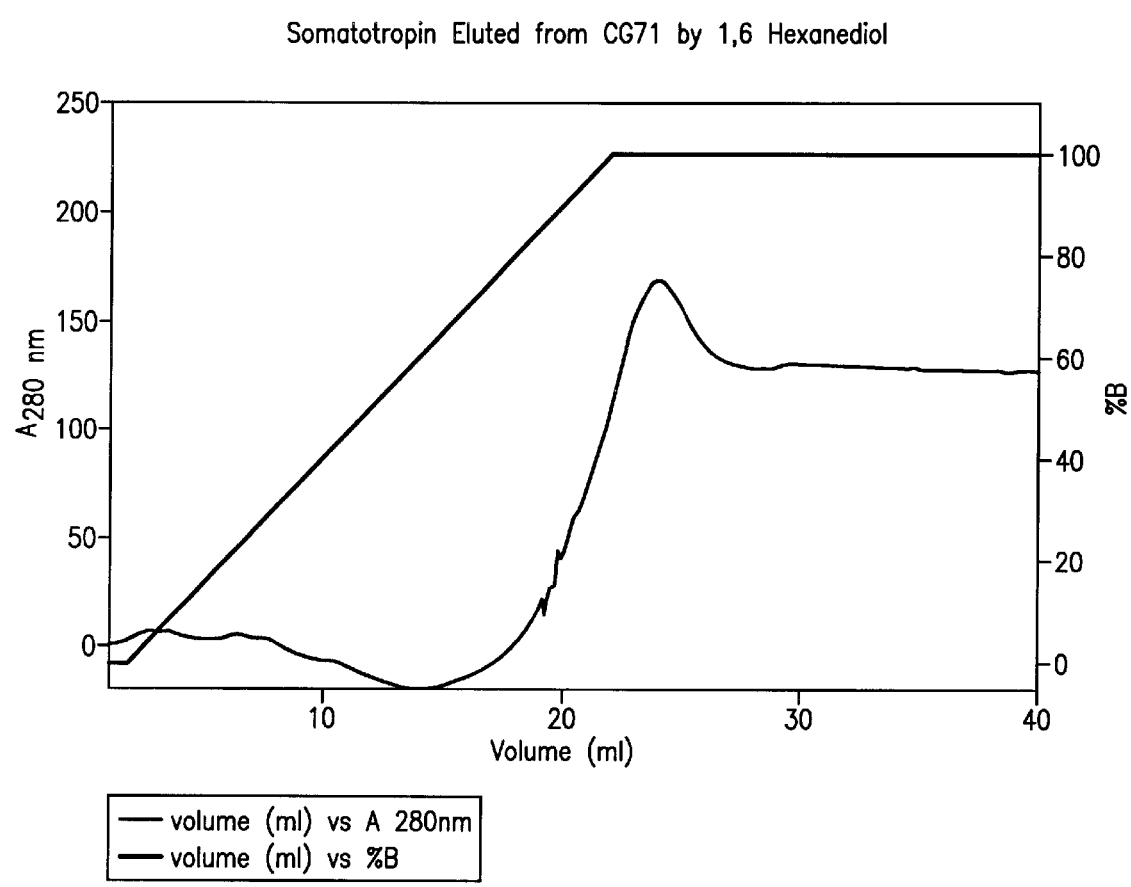
FIG. 24 illustrates the elution profile of somatotropin from a CG71-M column using a gradient of 0% to 50% 1,6 hexanediol in 50 mM Tris, pH 7.5.
Figure 25:
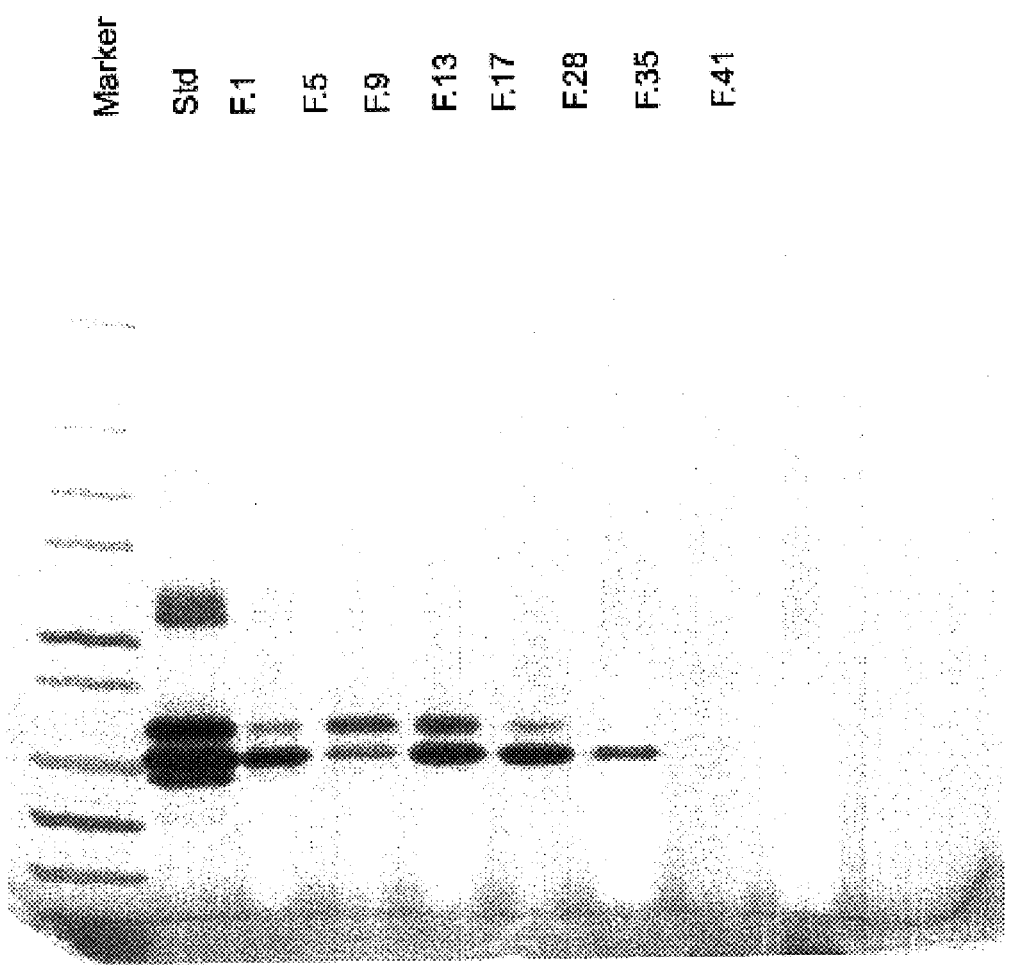
FIG. 25 illustrates SDS-PAGE analysis of the eluate of FIG. 24.

Somatotropin begins to elute when the solvent at the inlet of the CG71-M column is approximately 80% buffer B but was not fully eluted after 10 column volumes of 50% hexanediol (see, FIG. 24). The SDS-PAGE analysis indicates some fractionation within the peak (FIG. 25). C-4 RP-HPLC analysis does show the presence of other species but not in the amounts that the SDS-PAGE results suggest. It appears that the CG71-M column is fractionating different somatotropin species within the sample.

Figure 26:
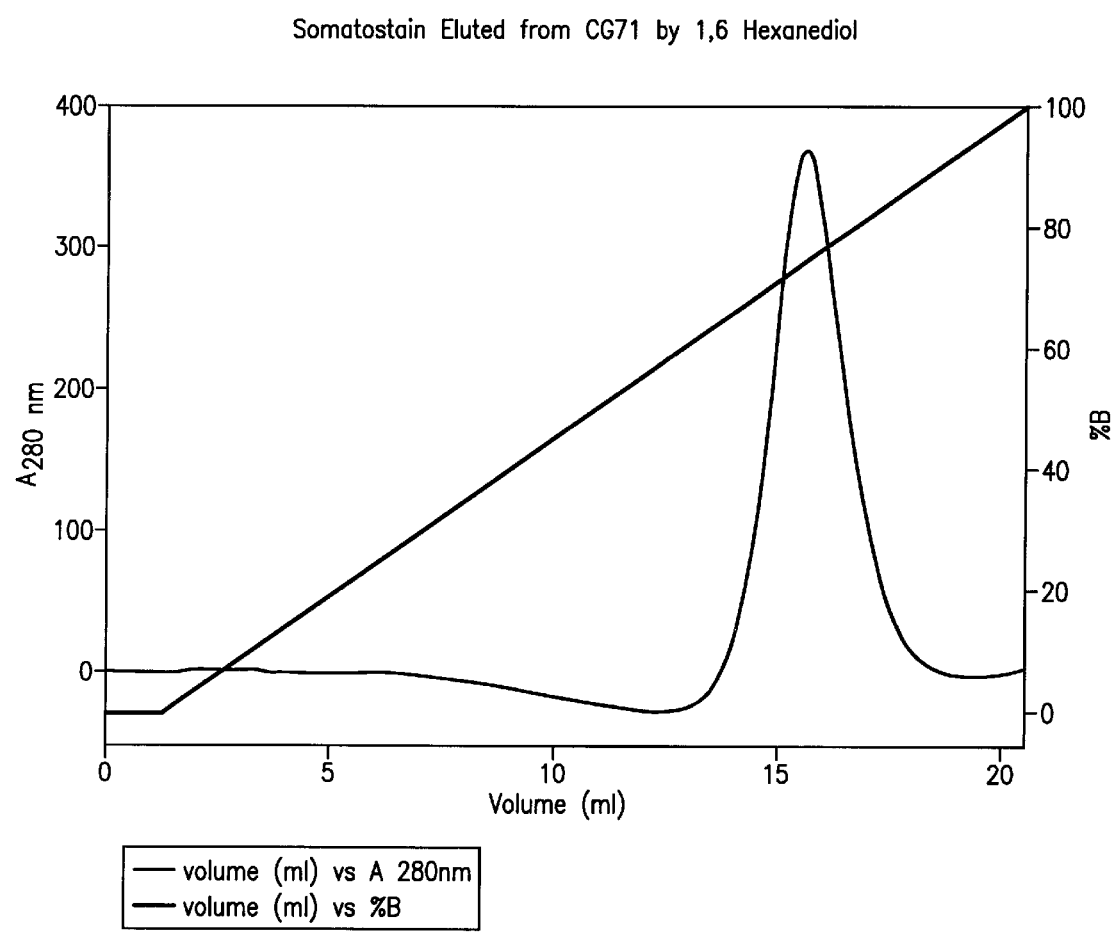
FIG. 26 illustrates the elution profile of somatostatin from a CG71-M column using a gradient of 0% to 50% 1,6 hexanediol in 50 mM Tris, pH 7.5.

Somatostatin elutes when the solvent at the inlet of the CG71-M column is approximately 66% B (FIG. 26). C-4 RP-HPLC analysis demonstrated the presence of somatostatin in the peak fraction.

Figure 27:
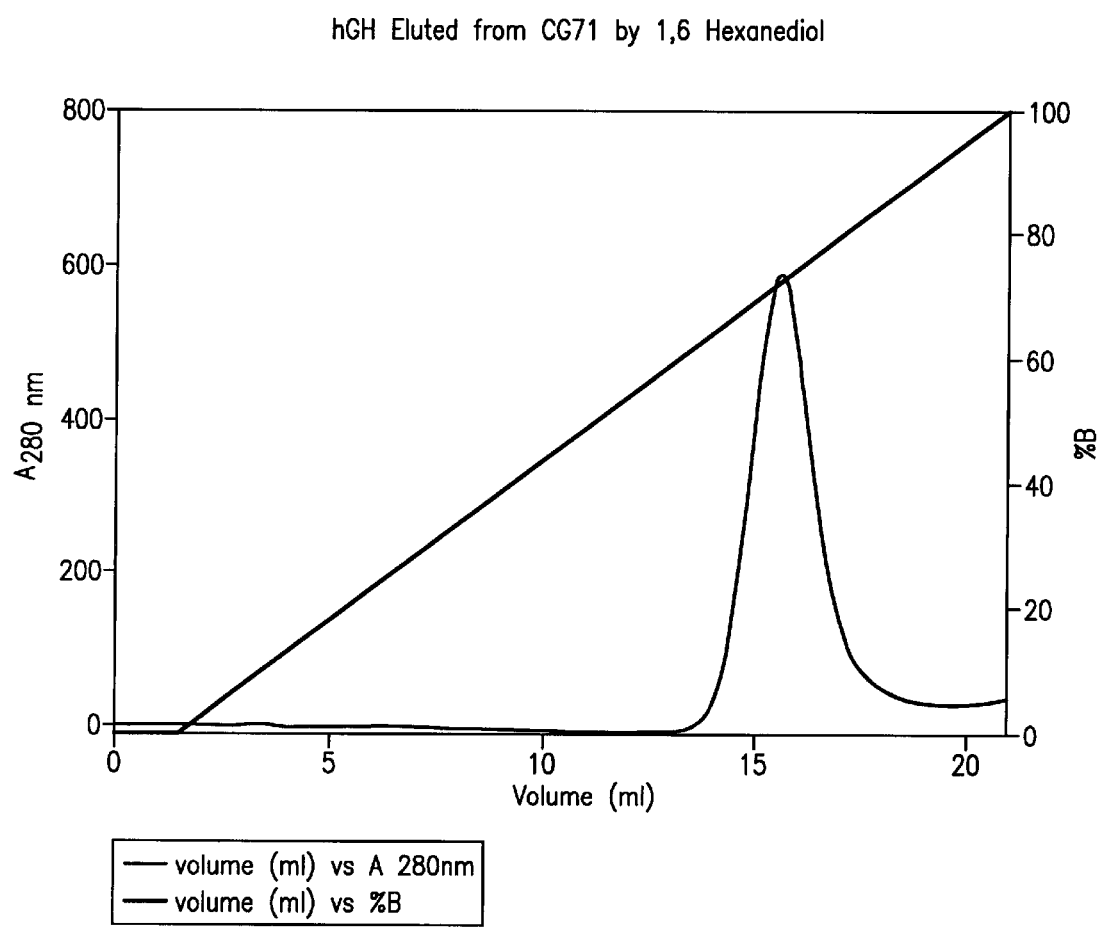
FIG. 27 illustrates the elution profile of hGH from a CG71-M column using a gradient of 0% to 50% 1,6 hexanediol in 50 mM Tris, pH 7.5.
Figure 28:
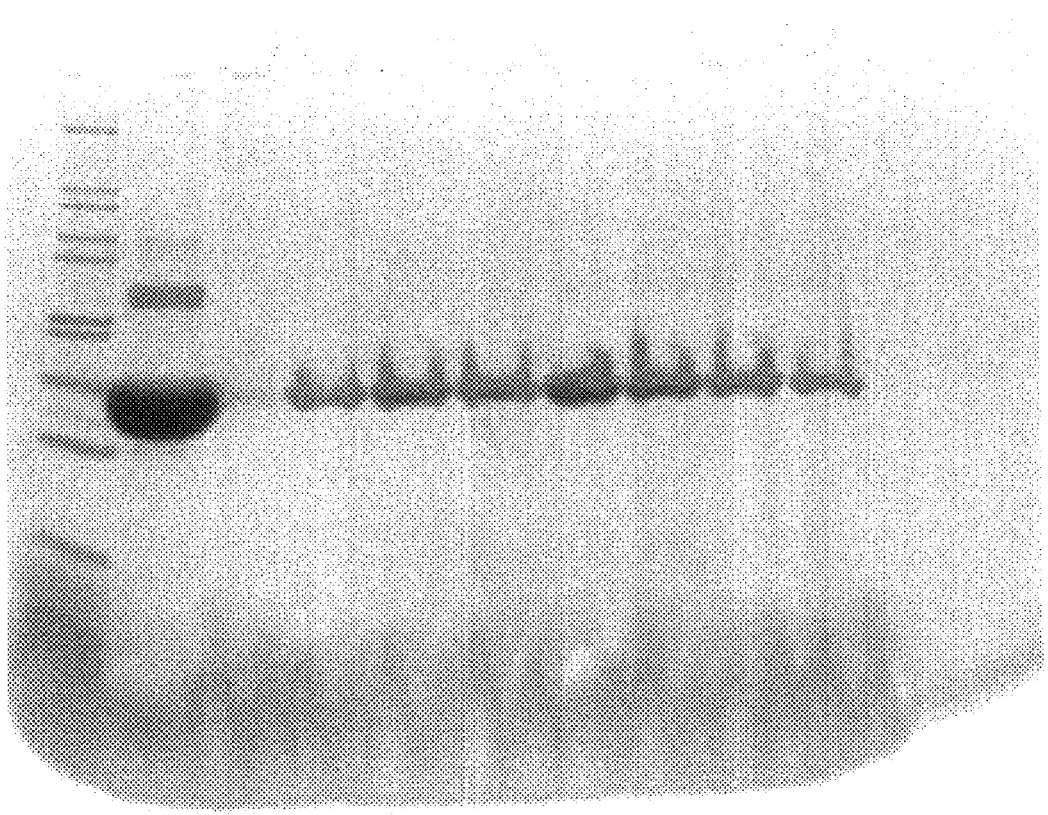
FIG. 28 illustrates SDS-PAGE analysis of the eluate of FIG. 27.

Human growth hormone elutes when the solvent at the inlet of the CG71-M column is approximately 60% B (FIG. 27). Human growth hormone is a single peak and appears to be homogeneous. The SDS-PAGE analysis (FIG. 28) shows that there are other components present. A shoulder comprising 5% of the total integrated area on the tailing edge of the main peak can be seen on the C-4 HPLC chromatogram.

The present invention is not to be limited in scope by the exemplified embodiments which are intended as illustrations of aspects of the invention and any aspects which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for purifying a molecule from a mixture comprising:
    loading the mixture onto a reverse phase liquid chromatography column; and
    eluting the molecule form the column with a buffer containing a diol selected from the group consisting of 1,5 pentanediol, 1,6 hexanediol and 1,7 heptanediol.

2. The method of claim 1, wherein the molecule is a polypeptide.

3. The method of claim 2, wherein the molecule is selected from the group consisting of human growth hormone and growth hormone antagonist.

4. The method of claim 1, wherein the molecule is a peptide.

5. The method of claim 1, wherein the peptide is selected from the group consisting of α-MSH, enkephalin, somatostatin and somatotropin.

6. The method of claim 1, wherein the diol is 1,6 hexanediol.

7. The method of claim 1, wherein the column is a high performance liquid chromatography column.

8. The method of claim 1, wherein the column is a preparative column.

9. The method of claim 1, wherein the column has a diameter of between about 5 cm and about 2.0 m.

10. The method of claim 9, wherein the column has a diameter of between about 10 cm and about 100 cm.

11. The method of claim 1, wherein the column includes a polymeric resin.

12. The method of claim 11, wherein the polymeric resin is styrene divinylbenzene.

13. The method of claim 11, wherein the polymeric resin is methacrylate or acrylic.

14. The method of claim 11, wherein the mixture is loaded on the column at between about 1.0 g molecule/liter bed volume and about 25.0 g molecule/liter bed volume.

15. The method of claim 3, wherein the polypeptide is growth hormone antagonist.

16. The method of claim 3, wherein the polypeptide is human growth hormone.

17. The method of claim 1, wherein the buffer is at a pH between about 2.0 and about 12.0.

18. The method of claim 17, wherein the buffer is at a pH between about 7.0 and about 11.0.

19. The method of claim 18, wherein the buffer is at a pH between about 6.0 and about 8.0.

20. The method of claim 7, wherein the concentration of 1,6 hexanediol in the buffer is between about 0% and about 80%.

21. The method of claim 20, wherein the concentration of 1,6 hexanediol in the buffer is between about 0% and about 50%.

22. The method of claim 1, further comprising further purification and/or processing of the molecule.

\* \* \* \* \*